United States Patent
Vetter

(10) Patent No.: US 9,808,226 B2
(45) Date of Patent: Nov. 7, 2017

(54) SOFT TISSUE CORING BIOPSY DEVICES AND METHODS

(71) Applicant: TRANSMED7, LLC, Portola Valley, CA (US)

(72) Inventor: James William Vetter, Portola Valley, CA (US)

(73) Assignee: TransMed7, LLC, Portola Valley, CA (US)

( * ) Notice: Subject to any disclaimer, the term of this patent is extended or adjusted under 35 U.S.C. 154(b) by 656 days.

(21) Appl. No.: 13/853,806

(22) Filed: Mar. 29, 2013

(65) Prior Publication Data

US 2014/0128769 A1    May 8, 2014

Related U.S. Application Data

(62) Division of application No. 13/651,393, filed on Oct. 13, 2012, now abandoned.

(60) Provisional application No. 61/547,678, filed on Oct. 15, 2011.

(51) Int. Cl.
| | |
|---|---|
| *A61B 10/02* | (2006.01) |
| *A61B 10/06* | (2006.01) |
| *A61B 17/32* | (2006.01) |
| *A61B 17/00* | (2006.01) |

(52) U.S. Cl.
CPC .......... *A61B 10/0266* (2013.01); *A61B 10/06* (2013.01); *A61B 10/0283* (2013.01); *A61B 2010/0225* (2013.01); *A61B 2017/00685* (2013.01); *A61B 2017/320064* (2013.01)

(58) Field of Classification Search
CPC ..... A61B 10/06; A61B 10/02; A61B 10/0266; A61B 2010/0225; A61B 2017/320064; A61B 17/320758; A61B 17/320016; A61B 17/32002; A61B 17/320092; A61B 2010/0208; A61B 10/0233; A61B 10/0283
USPC ................................ 600/562, 564, 566, 567
See application file for complete search history.

(56) References Cited

U.S. PATENT DOCUMENTS

| | | | |
|---|---|---|---|
| 1,493,240 | A | 5/1924 | Bohn |
| 2,751,908 | A | 6/1956 | Wallace |
| 4,522,206 | A | 6/1985 | Whipple et al. |
| 4,653,496 | A | 3/1987 | Bundy et al. |
| 4,682,606 | A | 7/1987 | DeCaprio |

(Continued)

FOREIGN PATENT DOCUMENTS

CA    2008190    7/1990

OTHER PUBLICATIONS

U.S. Office Action dated Apr. 10, 2015 in related U.S. Appl. No. 13/853,837.

(Continued)

*Primary Examiner* — David J McCrosky
(74) *Attorney, Agent, or Firm* — Young Law Firm, P.C.

(57) ABSTRACT

A biopsy device comprises a coring and transport assembly and a distal beak assembly. The distal beak assembly may be coupled to or near a distal end of the coring and transport assembly and may comprise at least one movable cutting element. The distal beak assembly may be configured to rotate about an axis, and assume at least a first open configuration operative to enable the at least one cutting element to core through tissue and a second closed configuration operative to enable the at least one cutting element to move through the tissue and to sever a cored specimen from the tissue.

14 Claims, 25 Drawing Sheets

(56) References Cited

U.S. PATENT DOCUMENTS

| | | |
|---|---|---|
| 5,052,402 A | 10/1991 | Bencini et al. |
| 5,074,311 A | 12/1991 | Hasson |
| 5,251,641 A * | 10/1993 | Xavier ............... A61B 10/0266 600/567 |
| 5,259,365 A | 11/1993 | Nishikori et al. |
| 5,507,296 A | 4/1996 | Bales et al. |
| 5,573,008 A | 11/1996 | Robinson et al. |
| 5,609,152 A | 3/1997 | Pellegrino et al. |
| 5,649,547 A | 7/1997 | Richart et al. |
| 5,762,069 A | 6/1998 | Kelleher et al. |
| 5,871,453 A | 2/1999 | Banik et al. |
| 5,976,164 A | 11/1999 | Bencini et al. |
| 6,083,237 A | 7/2000 | Huitema et al. |
| 6,086,543 A | 7/2000 | Anderson et al. |
| 6,139,508 A | 10/2000 | Simpson et al. |
| 6,142,957 A | 11/2000 | Diamond et al. |
| 6,149,607 A | 11/2000 | Simpson et al. |
| 6,193,673 B1 | 2/2001 | Viola et al. |
| 6,322,522 B1 | 11/2001 | Zimmon |
| 6,383,145 B1 | 5/2002 | Worm et al. |
| 6,391,043 B1 | 5/2002 | Moll et al. |
| 6,447,525 B2 | 9/2002 | Follmer et al. |
| 6,582,451 B1 | 6/2003 | Marucci et al. |
| 6,599,309 B1 | 7/2003 | Gilman |
| 7,008,381 B2 | 3/2006 | Janssens |
| 7,740,597 B2 | 6/2010 | Cicenas et al. |
| 7,762,960 B2 | 7/2010 | Timberlake et al. |
| 8,007,506 B2 | 8/2011 | To et al. |
| 8,133,237 B2 * | 3/2012 | Oostman, Jr. ...... A61B 10/0266 606/133 |
| 8,696,671 B2 * | 4/2014 | Solsberg ............ A61B 10/0275 606/205 |
| 8,939,963 B2 * | 1/2015 | Rogers ................... A61B 17/29 227/176.1 |
| 2001/0034495 A1 | 10/2001 | Wilson et al. |
| 2002/0165580 A1 | 11/2002 | Zwiefel et al. |
| 2003/0114773 A1 | 6/2003 | Janssens |
| 2004/0073139 A1 | 4/2004 | Hirsch et al. |
| 2005/0070885 A1 | 3/2005 | Nobis et al. |
| 2007/0219459 A1 | 9/2007 | Cohen |
| 2007/0255311 A1 | 11/2007 | Hiraoka |
| 2007/0270712 A1 | 11/2007 | Wiksell et al. |
| 2008/0046880 A1 | 2/2008 | Miller et al. |
| 2008/0221480 A1 | 9/2008 | Hibner et al. |
| 2009/0204023 A1 | 8/2009 | Goldenberg |
| 2009/0264910 A1 * | 10/2009 | Laufer ............ A61B 17/320068 606/169 |
| 2009/0287114 A1 | 11/2009 | Lee et al. |
| 2009/0299220 A1 | 12/2009 | Field et al. |
| 2010/0078296 A1 | 4/2010 | Lapeyre et al. |
| 2010/0121153 A1 | 5/2010 | To |
| 2010/0312141 A1 | 12/2010 | Keast et al. |
| 2011/0125054 A1 | 5/2011 | Clements et al. |
| 2011/0132961 A1 | 6/2011 | Whitman et al. |
| 2011/0245716 A1 | 10/2011 | Flatland et al. |
| 2013/0190651 A1 | 7/2013 | Vetter |
| 2014/0142602 A1 | 5/2014 | Polo |

OTHER PUBLICATIONS

U.S. Office Action dated May 5, 2015 in related U.S. Appl. No. 13/973,898.
U.S. Office Action dated Jun. 19, 2015 in related U.S. Appl. No. 13/853,719.
U.S. Office Action dated Apr. 10, 2015 in related U.S. Appl. No. 13/651,393.
U.S. Office Action of Feb. 3, 2015 in related U.S. Appl. No. 13/973,898.
International Search Report dated Feb. 26, 2013 in PCT/US12/60149.
Written Opinion of the International Searching Authority dated Feb. 26, 2013 in PCT/US12/60149.
U.S. Office Action dated Apr. 13, 2015 in related U.S. Appl. No. 13/853,768.
U.S. Office Action dated Feb. 3, 2015 in related U.S. Appl. No. 13/973,898.
U.S. Office Action date Apr. 10, 2015 in related U.S. Appl. No. 13/853,636.
International Search Report and Written Opinion of International Searching Authority dated Apr. 16, 2015 in related PCT application PCT/US14/51945.
European Patent Office Extended Search Report dated Mar. 20, 2015 in related EP patent application 12839250.3.
International Search Report and Written Opinion of International Searching Authority dated Mar. 11, 2015 in related PCT application PCT/US14/55190.
International Search Report and Written Opinion of International Searching Authority dated Mar. 23, 2015 in related PCT application PCT/US14/39676.
International Search Report and Written Opinion of International Searching Authority dated Apr. 23, 2015 in related PCT application PCT/US14/39668.
U.S. Office Action dated Jan. 16, 2015 is related U.S. Appl. No. 13/651,393.

* cited by examiner

SOFT TISSUE CORING BIOPSY DEVICES AND METHODS

CROSS REFERENCE TO RELATED APPLICATIONS

The present application claims priority to co-pending and commonly assigned U.S. patent application Ser. No. 13/651,393 filed on Oct. 13, 2012, which application claims priority to U.S. provisional patent application Ser. No. 61/547,678 filed on Oct. 15, 2011, which applications are hereby incorporated herein in their entirety.

BACKGROUND

Embodiments relate to medical devices and methods. More particularly, embodiments relate to single insertion, multiple sample soft tissue biopsy and coring devices and corresponding methods for retrieving multiple soft tissue biopsy samples using a single insertion.

SUMMARY

Embodiments are drawn to various medical devices and methods that are used for core biopsy procedures. According to one embodiment, a biopsy coring/delivery device may be configured to retrieve multiple samples of normal and/or abnormal appearing tissues during a single insertion through the skin (percutaneous procedure) into the, for example, soft tissue area of the body from which the biopsy is taken. Embodiments may comprise structures and functionality for different phases of a multi-phase biopsy procedure. For example, embodiments may comprise a pre-treatment of the area and/or of the abnormal tissue, or the delivery of tracer materials for tracking the potential spread or flow patterns whereby the abnormal tissues (such as cancerous tissues) may metastasize. Embodiments may also comprise an intra-procedure delivery of medications that may anesthetize tissues at the site, or the delivery of other therapeutic agents such as pro-coagulants and others, as well as delivery of post-procedure materials such as medications, implantable materials for cosmetic purposes and other implantable elements such as marking devices for later imaging reference. Embodiments of a biopsy device, along with associated related subcomponents described herein, may provide the capability to retrieve solid, contiguous and/or fragmented tissues as well as liquid and semi-solid tissues for analysis, diagnosis and treatment. Embodiments may be configured to be portable, disposable or reusable and may be electrically, mechanically and/or manually powered and operated.

DETAILED DESCRIPTION

Figure 1:
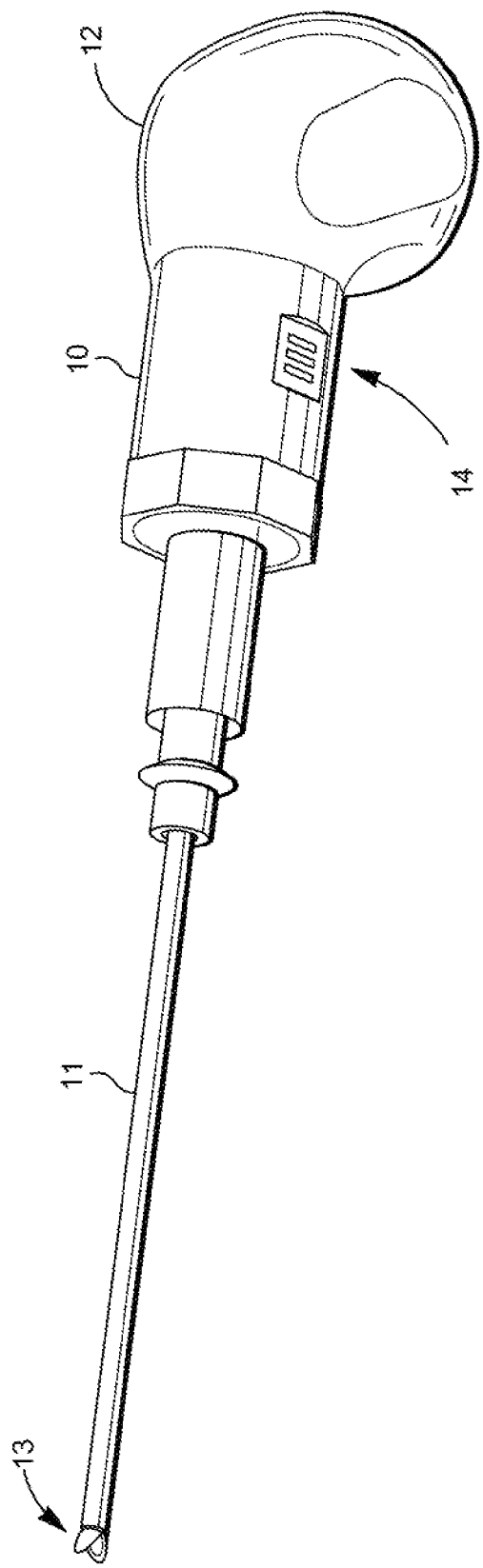
FIG. 1 is a perspective view of a core biopsy device according to embodiments.

Reference will now be made in detail to the construction and operation of preferred implementations of the embodiments illustrated in the accompanying drawings. The following description is only exemplary of the embodiments described and shown herein. The embodiments, therefore, are not limited to these implementations, but may be realized by other implementations.

Core biopsy procedures have evolved from simple core needle biopsies comprising aspiration of fluids using a simple syringe and needle to devices having the capability to extract solid tissues for histopathological analysis. This more recent capability has proved to be a far more powerful way to diagnose diseases and abnormal tissue entities, some of which are extremely life threatening, and others which may be more benign but nevertheless must be definitively distinguished from the more dangerous types of abnormalities, including cancerous and pre-cancerous lesions, in-situ cancers, invasive cancers, benign space occupying lesions, cystic lesions and others. As core biopsy procedures have evolved into far more diagnostically powerful tools, they have displaced many of the more invasive open surgical procedures, which had been and continue to be performed for diagnostic purposes, based on the advantages of retrieving a sufficient volume of tissue with the preserved architecture that is so critical in the diagnosis and treatment algorithm used by clinicians in addressing these abnormalities and diseases. One of the most critical needs during a biopsy procedure is to accurately correlate tissue diagnosis with imaging diagnosis. In order to successfully accomplish this, it is essential to know that the retrieved tissue actually and accurately represents the imaged abnormality. This is an aspect where many conventional coring devices fall short. For this reason, open surgical diagnostic procedures and other invasive procedures continue to be performed. Other clinically significant limitations of these procedures include the manner in which the abnormal tissue is separated from the host organ, the manner in which the tissue is retrieved and handled during the process by the coring biopsy device, and the amount of biopsy artifact/damage imparted to the tissue specimens by the coring procedure and device. Yet another consideration in the design of improved coring devices is the existence of an important tradeoff among conventional coring biopsy devices. It is well known that the larger the caliber of the retrieved tissue samples, the better the correlation with the imaging abnormality, and thus the easier, more accurate, definitive and helpful the diagnosis. However, in order to retrieve larger caliber specimens, most biopsy devices have large outer diameters, leading to increased trauma, complications, pain and other adverse effects, due principally to the imprecision associated with such large bore devices. Additionally, tracking a large bore device through the tissues is much more difficult, particularly without the help of an active mechanism to aid in smoother and more gradual advancement of the biopsy device. The larger the caliber of the biopsy device, the more difficult it becomes to precisely visualize the biopsy device in relation to the target abnormality, especially for small lesions (on the order of about ½ cm to less than ¼ cm). Today, more than 4-5 million diagnostic core biopsies are performed each year around the world in the breast alone, with as many as 2 million diagnostic breast biopsies being performed each year in the US. There is little doubt that many invasive, open surgical diagnostic biopsies should be replaced by improved core biopsy procedures. Moreover, there is a need to improve upon existing core biopsy procedures and devices by eliminating the well-known limitations of current devices.

Figure 2:
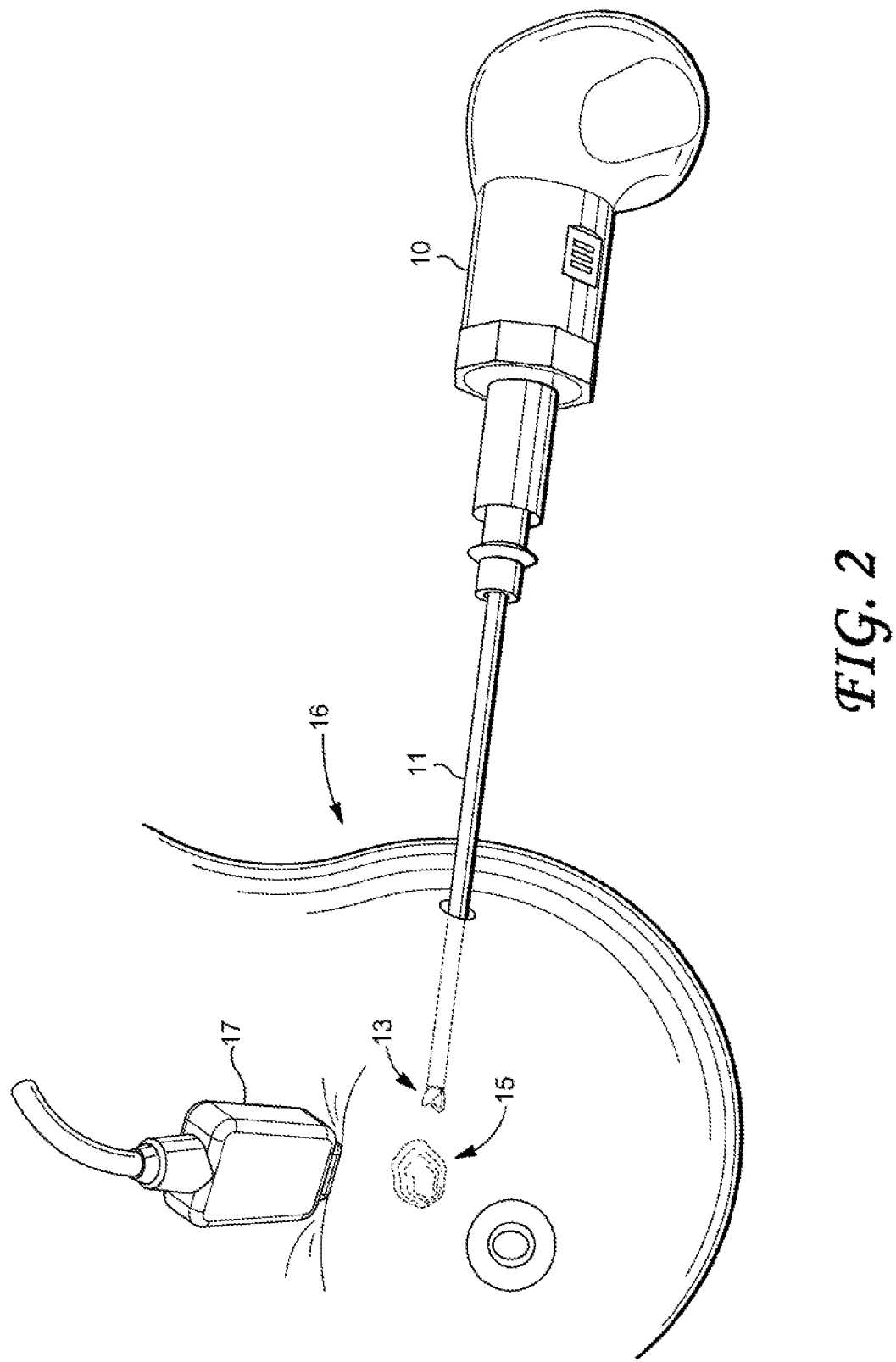
FIG. 2 is a perspective view of a core biopsy device according to one embodiment.

Reference will now be made in detail to the construction and operation of preferred implementations illustrated in the accompanying drawings. FIGS. 1 and 2 show a biopsy device 10 according to embodiments having a tubular coring and transport assembly 11 of appropriate dimensions to retrieve a single or multiple core samples of tissue (not shown) that is/are sufficient to provide the desired clinical diagnostic or therapeutic result. Such an appropriate dimension may be, for example, about 4½ inches in length, in addition to a forward excursion of the tubular coring and transport assembly 11 during the coring phase. It is to be understood, however, that the foregoing dimensions and any dimensions referred to herein are exemplary in nature only. Those of skill in this art will recognize that other dimensions and/or configurations may be implemented, depending upon the envisaged application, and that the tubular coring assembly could be of any length, and may be configured to be bendable so as to define a curve. One embodiment of the biopsy device 10, as shown in the figures, may be implemented in a hand-held configuration comprising an ergonomically comfortable and secure handle 12 at its proximal end from which the tubular coring and transport assembly 11 extends so that the biopsy device 10 may be easily directed with one hand while the other hand is free to hold a guiding probe such as an ultrasound transducer (shown in FIG. 2). However, it is to be understood that embodiments may readily be configured to fit onto any number of guiding devices such as a stereotactic imaging stage or other guidance modality (not shown). As shown, one embodiment of the biopsy device 10 may comprise a plurality of sharp, rotating cutting elements 13 (herein, alternatively and collectively referred to as "beak", "beak assembly" or "beak element" or "beak elements") projecting forward distally from the distal free end of the tubular coring and transport assembly 11 for the purpose of forward penetration, coring and/or parting off of the core sample. The tubular coring and transport assembly 11 may comprise a plurality of components, which plurality of elements may be configured to transmit rotational movement to the rotating or non-rotating cutting elements 13. It is to be understood that the "tubular" description of the coring and transport assembly may be of any cross section shape and size, of any length. The components of the tubular coring and transport assembly 11 (not all components being visible in FIGS. 1-2) also transfer the core sample back proximally along the internal length of the tubular coring and transport assembly 11 to the handle 12 and storage compartment (not shown). According to one embodiment thereof, the biopsy device 10 may comprise a handle or handle 12, which handle or handle 12 may comprise and/or be coupled to mechanical components (not shown) needed to drive the coring/transport/part-off/delivery distal tubular coring and transport assembly 11. As shown, one embodiment may comprise a distally-disposed beak 13 that may comprise one or more sharp cutting tip blades configured to penetrate to the target site 15 of the intended biopsy, core the target tissue and part-off or cut off the core sample (not shown) at its base. The handle 12 may also be coupled to and/or comprise the mechanical components needed to drive the transport mechanism within the distal tubular coring and transport assembly 11 and also within the handle and through to a storage magazine (not shown) attached to the proximal end of the handle 12. The ability of the present biopsy device to repeatedly core and retrieve multiple samples (not shown) during a single insertion, store the cored samples in a magazine (not shown) means that with a single penetration through the skin of, for example, a human breast 16, the operator can sample multiple areas without causing additional trauma that would be associated with having to remove the biopsy device 10 each time a sample is taken, and reintroducing the biopsy device 10 back into the patient to take additional core samples. The handle 12 may also contain and/or be coupled to (internal or external) mechanical components (not shown) for augmentation vacuum fluid evacuation as well as the delivery of materials such as a variety of medications, tracer materials and/or implantable marker elements (not shown here). The distal or tubular coring and transport assembly 11, according to one embodiment, may be configured such as to create the smallest possible caliber (e.g., diameter) of coring tube (tubular coring and transport assembly 11) with a range of (for example) about 16 gauge to about 10 gauge diameter, while providing a sufficiently large diameter of core sample to be clinically useful. The tubular coring and transport assembly 11 may also be of a sufficient length to reach distant target sites such as, for example, about 4½ inches (11 centimeters) from the skin surface without the need for a surgical procedure to enable the distal end (that end thereof that is furthest from the handle 12) of the biopsy device 10 to reach the targeted site. As shown in the embodiments of FIGS. 1 and 2, the distal tubular coring and transport assembly 11 of the biopsy device 10 may extend distally from the handle 12 a distance sufficient to create a core (not shown) of usable length for diagnosis and/or treatment purposes. As is described below, this distance of forward or distal projection can be selectively changed at will, thanks to structure configured for that purpose, which may be built into or otherwise coupled to the present biopsy device 10. Embodiments of the present biopsy device 10 may be used by right and/or left handed persons and in multiple positions (including upside down for example) and orientations (different angles), so that in areas of limited access, the present biopsy device may still be easily positioned for ideal orientation to perform a biopsy procedure under real time or other image guidance (not shown). The entire device may be configured to be disposable or may be configured to be reusable in whole or in part. Embodiments of the present biopsy device 10 may be electrically powered by one or more batteries (not shown) stored, for example, in the handle 12 and/or external power sources (not shown) through a simple electrical coupling (not shown) to connect to an external power supply conveniently placed, for example, in the handle or proximal end of the present biopsy device. The biopsy device 10 may alternatively in whole or in part, be powered by mechanical energy (provided, for example, by compressed air motors, by watch-type springs, or manually by the operator). In FIGS. 1-2, the biopsy device 10 is shown in a coring configuration with the distal end thereof open for coring, and in a configuration in which it may be partially projecting forward from the proximal handle 12, from its resting position with a portion of the tubular coring and transport assembly 11 extending slightly distally along the first part of its forward excursion. In this view, the biopsy device 10 is shown with a combination switch 14 to activate and/or physically move various internal components (not shown).

FIG. 2 is a perspective view of the core biopsy device according to one embodiment, with the distal tip (comprising the beak assembly) of the biopsy device in position inside an organ such as a breast, a target lesion, an ultrasound probe on the surface of a breast, and rotating cutting and coring beak assembly in an open position, according to embodiments. FIG. 2 shows the coring biopsy device 10 pointing at a target lesion 15 within breast tissue 16, as visualized under an ultrasound guiding probe, shown at reference numeral 17. The present biopsy device's tubular coring and transport assembly 11 is shown pictorially as if moving in an axially forward direction with its distally placed, sharp cutting tip blades of the beak 13 open and rotating for coring.

According to one embodiment, a method of carrying out a biopsy procedure may comprise imaging the tissue of the organ (such as the breast) of interest and identifying the target lesion(s). The skin may then be cleaned using sterile techniques, the patient may be draped and anesthetics may be delivered. The distal tip of the present biopsy device may then be introduced through a skin nick. For example, a penetration mode may be activated, in which the distal beak may be caused to assume a closed beak configuration. The distal beak 13 may be caused to rotate to facilitate penetration through the tissue. The distal beak 13 may then be advanced toward the target lesion and may then be caused to stop just short (e.g., 2-4 mm) of the nearest edge of the target lesion. A stage may then be initiated in which the distal beak 13 may be caused to assume an (e.g., fully) open configuration and then stopped. An optional delivery stage may then be initiated, to deliver, for example, the contents of a preloaded cartridge such as tracer elements like visible dyes, echo-enhancing materials and/or radioactive tracer elements or others such as medications (which may be delivered at any stage of the biopsy procedure). After or instead of optional injection stage, a coring stage may be initiated while holding the biopsy device handle steady and/or actively redirecting the distal beak as desired. The coring may then continue, in either an automatic or semiautomatic mode. During the coring stage, the carriage movement function may be engaged to either elongate or shorten the axial excursion of the coring elements as desired to achieve acceptable or desired tissue margin collection at both ends of sample, or to avoid unwanted coring into adjacent tissues, or simply to obtain differing core sample lengths for later correlation with various stages of the documented procedure. During one or more of the corings, a record stage may be activated to halt the coring stage just after the specimen has been parted-off in order to enable the practitioner to record image(s) of the shaft of the biopsy device in place in the lesion, to document that core samples (particularly those of different chosen lengths obtained serially during the procedure) were acquired precisely from imaged lesions. Upon completion of the biopsy procedure and, if desired, prior to removal of the device, a specimen ultrasound or a radiograph may be carried out upon the specimens collected within the storage magazine, which may be especially configured for echo and radio lucency as well as MRI-compatibility. The removable magazine may then be placed into a receptacle preloaded with preservative and sealed, and if desired, a replacement magazine may be loaded into the device to continue the biopsy. Following the acquisition of a sufficient number of core samples and following the documentation stage, the core sample acquisition site may be firmly correlated with the image abnormality location. If so attached, the liquid aspirate storage vessel may then be removed and capped securely for transport to an appropriate laboratory for cellular and subcellular analysis. Alternatively, still with the biopsy device in place, the tissue storage magazine may be removed, which may be replaced with an injection cartridge that may be pre-loaded with post-biopsy elements such as medications, cosmetic implants, brachytherapy elements, and the like. The present biopsy device may then be removed from the site and the wound may then be dressed, with the usual standard of care procedures. It is to be understood that the above description is but one exemplary methodology and that one or more of the steps described above may be omitted, while other steps may be added thereto. The order of some of the steps may be changed, according to the procedure.

Figure 3:
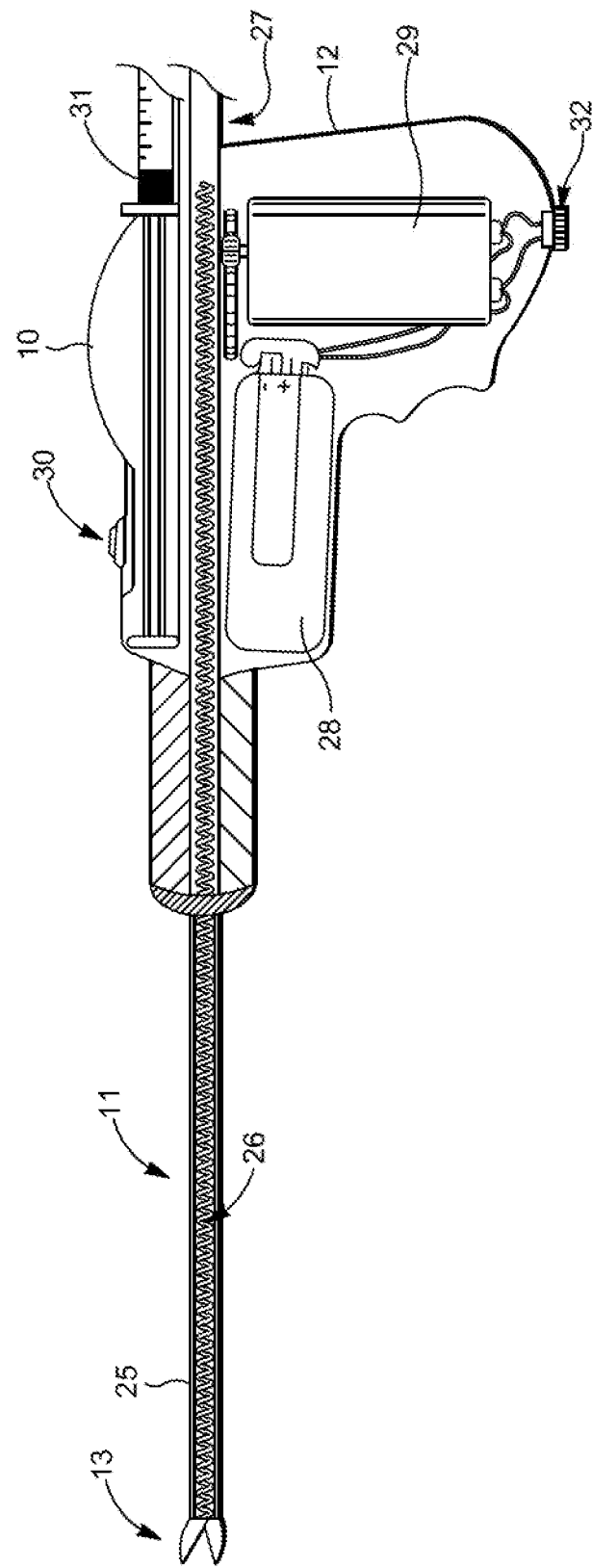
FIG. 3 is a side view of the core biopsy device of FIG. 1, showing internal components thereof, according to embodiments.

FIG. 3 shows a side internal view of a coring biopsy device 10, according to one embodiment. As shown, two internal components of the present biopsy device's tubular coring and transport assembly 11 are shown; namely, a non- or differentially rotating outer tubular element 25 of the transporting mechanism and a more internally placed (also non- or differentially rotating) helical component 26 extending from the sharp cutting tip blades of beak 13 proximally back through the handle 12 and ending in overlapping manner inside or outside up to the opening of a storage magazine 27. Also shown are a battery power source 28 and an electrical driving motor assembly 29 including gearing configured to rotate and axially displace the components of the tubular coring and transport assembly 11. In the embodiment illustrated in FIG. 3, an activating switch 30 is shown in position at the forward, topside portion of the handle 12, it being understood that the placement and structure thereof may be freely selected. An augmenting vacuum/delivery mechanism may also be provided, as shown at reference numeral 31, which may also be driven by the driving motor assembly 29 during coring and transport of the core tissue specimens (not shown). Also shown in FIG. 3 is a power coupling or jack 32, configured for connection to an external power source (not shown).

Figure 4:
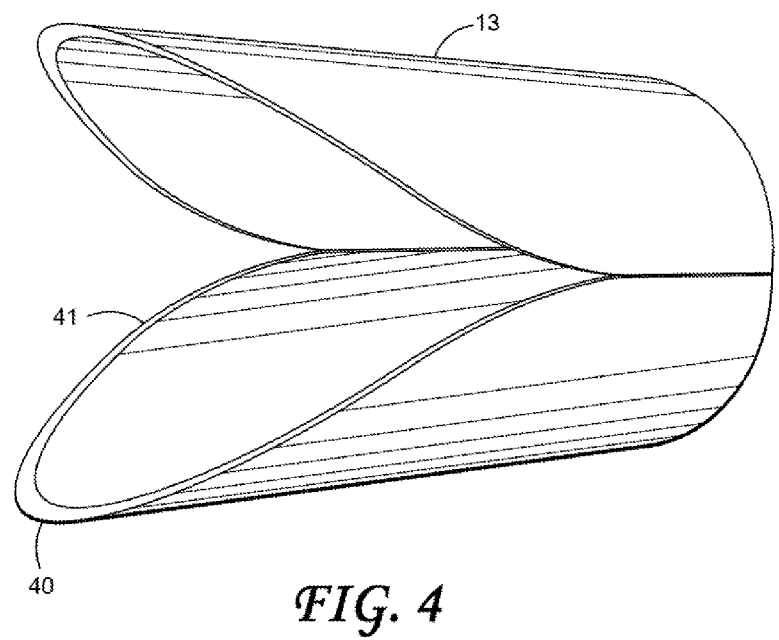
FIG. 4 is a perspective view of a beak assembly of the core biopsy device of FIG. 1 in an open, coring and/or delivery position, according to embodiments.

FIG. 4 shows a close up perspective view of sharp cutting tip blades emerging from the distal end of the tubular coring and transport assembly 11, which may be advantageously configured, according to one embodiment, to have a beak-like shape. The forward and side edges 40 and 41 of the blades may be sharpened such that they are able to cut tissues while the beak assembly rotates, while moving distally in an axial direction with respect to handle 12, and/or while opening away from and then, in sequence, closing down against one another to part-off or sever the core sample (not shown). The cutting tips/blades of beak assembly 13 may be opened as far apart as desired. However, for illustrative purposes, they are shown in FIG. 4 as being opened to a position that may be characterized as being roughly parallel to the rest of the tubular coring and transport assembly 11 (not shown in FIG. 4). The shape of these cutting tip blades of beak assembly 13 may be advantageously selected such that when closed, they completely occlude along their forward 40 and side 41 edges. However, the cutting tip blades of beak assembly 13 need not completely contact one another along the entire edges in order to effectively core and sever or part-off the base attachment end of the core sample (not shown), as, for illustration purposes only, if the beaks are rotating or moving axially while closing. The shape of the sharp cutting elements of beak assembly 13 may be formed, for example, by straight angle cutting of a tube such as stainless steel hypo-tube, similar to the way a hypodermic needle is made, but with a significant differentiator; namely, that the cutting of the elements of beak assembly 13 may be advantageously carried out such that the first angle or bevel cut is stopped at the halfway point along the cut, once the midway point across the tube diameter is reached. Then, beginning from the opposite sidewall of the tube, another identical cut is made at the same angle and beginning in the same plane and starting point. This cut ends where it would meet the initial cut (if using the same raw stock tube for example). In this manner, the edges of the cutting tip elements would perfectly occlude and close off completely with one another all along the forward 40 and side 41 cutting surfaces, while in the closed, part-off/severing position (not shown). According to an embodiment, a method for shaping the sharp cutting elements of beak assembly 13 may comprise an additional angle or bevel cut away from the sharp tip end of the cutting element. This cut begins more near the sharp tip end than straight across the diameter of the raw stock tube or hypo-tube stock. The purpose of beginning this cut "downstream" towards the tip is so that in closed position, the distance chosen permits the closed elements of beak assembly 13 to close down without their bases extending outward beyond the diameter of the tube from whence they were taken—which may be about the same diameter of other components of biopsy device 10, such as the outer non- or differentially rotating outer tubular element 25. It may also be advantageous to cut the cutting tip elements from a tube of slightly larger diameter than the other components of the present biopsy device to achieve shapes that would still comprise all of the functionality of the design, but also comprise a feature such as a "springiness" to simplify the hinge mechanisms in nested form, simplify construction, allow additional tip base configurations, or allow steeper angles for the cutting tip in closed configuration or to allow the beaks to open to such a degree that the cutting radius of the beak tips exceeds the outer diameter of the outer tubular element 25. Such inherent springiness would also improve the stiffness of the cutting tips in a radial dimension, which may facilitate easier penetration of dense tissues. The base cut may, however, comprise a flap (and thus require a slightly more complex cut to create a slightly more detailed shape to comprise a contiguous section that may be formed into a hinge as described (not shown) above that may later be made into a hinge (such as is shown below, with respect to hinge assembly 50 in FIG. 24).

The shape of the sharp cutting elements beak assembly 13, such as the embodiment thereof shown in FIG. 4, for example, provides substantial support vectors for all movements required of the cutting blades during rotation, opening/closing and axial motions (not shown). This embodiment enables the sharp cutting elements of beak assembly 13 to be made extremely thin, which fulfills a requirement that for any given outer radial dimension of the tubular coring and transport assembly (including the cutting beak assembly) 11 (see also FIG. 1), the caliber of the core sample retrieved from the patient will be a large as possible. In addition, were the sharp cutting elements of beak assembly 13 instead formed of a cone-like shape, they would not, when wide open and roughly parallel to the long axis of tubular coring and transport assembly 11, core a full diameter sample, since the conical taper progressing towards the tip would be of ever diminishing radius compared with the tubular coring and transport assembly 11, which is prepared to receive the core sample. The shape(s) of the sharp cutting elements of beak assembly 13 specified for use in coring and part-off according to embodiments enable the biopsy device 10 to core a full diameter (and in fact larger than full diameter with respect to the dimensions of the coring and transport assembly 11, of which slightly larger caliber (e.g., diameter) may be desirable in order to compress, "stuff", or pack in as much tissue sample into the tubular coring and transport assembly 11 as possible), which may prove advantageous from several standpoints (including diagnostic, clinical standpoints) or provide more sample (not shown) for analysis.

Figure 5:
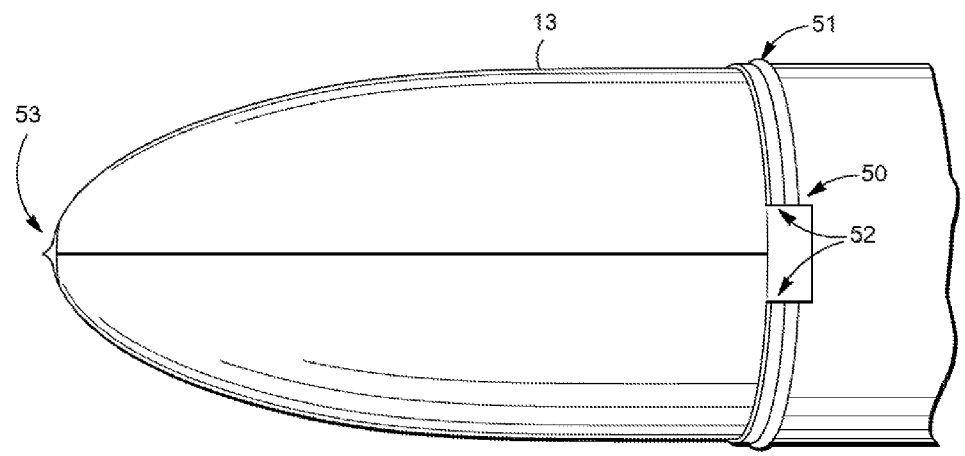
FIG. 5 is a top view of a beak assembly of the core biopsy device of FIG. 1 in a closed, penetration or part-off position, according to embodiments.

FIG. 5 shows a top view of the sharp cutting elements of beak assembly 13, according to one embodiment. In this view, a hinge assembly 50 (which may have been formed continuous with the rest of the piece, using, during construction, a slightly more complex cut from the raw tube stock as described above) is shown at the proximal junction point of the sharp cutting elements of beak assembly 13 with the non- or differentially rotating outer tubular element 25 of a tubular coring and transport assembly 11 (shown in FIG. 1). The hinge assembly 50 may interact with a raised rim section 51, or with other attachment method that permits differential rotation of the outer tubular element 25, so that the beak assembly 13 may rotate independently of the outer tubular element 25 of the tubular coring and transport assembly 1. It is to be understood that this hinge assembly may also be fixed to the outer tubular element 25, and thus rotate the beak assembly contiguously with the outer tubular element. This hinge assembly 50 may have sharpened edges 52 so that they encounter minimal resistance in the tissue during rotational and other movements. This design feature may also serve to "core" a slightly larger diameter within the tissue during "closed beak penetration" mode, so that the tubular coring and transport assembly 11 may move with less resistance within the tissue environment on the way to the target lesion or tissue harvesting site. The constituent elements of the hinge assembly 50 may also be slightly angled so that, during rotation, they provide a "screw" type effect, helping to pull the outer diameter of the shaft (tubular coring and transport assembly 11) through the dense tissues that are often encountered in breast tissue 16 (shown in FIG. 2) or other tissue found in the body, on approach to target lesion 15 (also shown in FIG. 2).

Clinically and procedurally, the ability of a biopsy device to advance gently towards a target lesion provides several advantages. Indeed, when a biopsy device does not advance gently toward a target lesion or does not smoothly core through dense target tissue, the operator may be led to exert excessive force onto the biopsy device, thereby potentially forcing the biopsy device into and even through adjacent structures. There have been instances of biopsy device components being broken off, requiring surgical removal thereof from the biopsy site when excessive force was needed in attempts to obtain core samples from tissues such as dense breast tissue 16 (the density characteristics of the breast tissue 16 not illustrated in FIG. 2). The present method of powered, closed beak penetration mode in one embodiment herein and provided for with a specific cycle stage in the biopsy device 10 of FIG. 1, enables an operator to gently and smoothly approach a target lesion such as shown at 15 in FIG. 2, without requiring excessive manual axially-directed force to be exerted on the present biopsy device by the operator. It is to be noted that when excessive force must be exerted to advance conventional coring devices through dense tissue, the resultant image provided by guidance modalities (such as ultrasound) may be significantly distorted by the force applied to the conventional coring device and transferred to the surrounding tissue. This force may damage tissue, resulting in loss of tissue architecture and production of the aforementioned biopsy artifact, and may also cause the resultant image to be less distinct or blurred which, in turn, makes the biopsy procedure less accurate and much more difficult technically. It is an important goal of all core biopsy procedures to firmly establish that the core sample is taken from the highly specific image area, notwithstanding the constraints imposed by the small dimensions of the target tissue. Such small dimensions, therefore, require clear views of sharp margins to attain the kind of accuracy desired.

Keeping the foregoing in mind, embodiments provide the operator with methods and mechanisms to gently approach and core a target lesion with minimal physical, manual force, thus freeing the operator to focus on the (often minute) structures to be sampled. In core biopsy procedures, it is highly useful to capture a small amount of normal surrounding tissue still attached to the abnormal tissue, at the junction there between, and on both ends of the core sample. The present devices and methods provide an opportunity to accurately measure the size of an abnormality optically, for example, under microscopic analysis. The embodiment of the core biopsy device may be configured to gently approach the target lesion 15 in a closed beak configuration (i.e., a configuration substantially as shown in FIG. 5), stopping just short of target lesion 15, then proceeding to an open beak configuration (i.e., a configuration substantially as shown in FIG. 4), coring a small bit of normal adjacent tissue, continuing through lesion 15 to the distal side thereof and coring a small amount of normal tissue on the other side of the lesion 15 as well, still controllably within surrounding host tissue such as breast tissue 16. Though not illustrated here, the hinge assembly(ies) 50 may also interact with a flared outward/flared inward circumferential inner surface of the outer tubular element 25 for the purpose of providing a hinge assembly for the rotating, cutting, sharp cutting elements of beak assembly 13. As shown, the rotating, cutting, part-off beak assembly 13 may have additional shapes such as a more pointed end as shown (arrow at reference numeral 53) at the forward tip, and/or may have serrations along one or more edges to facilitate cutting, part-off, opening and/or closing. The rotating, cutting, part-off beak assembly 13 may also have a more tapered (steeper or shallower angles) shape as required by the confines of and resistance of the materials in which they are designed to operate. Such different shapes (including asymmetric shapes) and sharpened tips (such as point(s) 53) are considered to be within the scope of the present embodiments. Embodiments, including the beak assembly 13, may be configured to enable the coring of full diameter samples and the parting-off of the cored full diameter sample. Embodiments may be further configured for closed and/or open beak penetration through tissue and for transporting the core sample (slightly larger diameter cores, tapered ends for streamlined passage of cores, etc.,) among other functions. Embodiments may also be configured for open beak coring to a target tissue, enabling a gentle "core to the lesion" operation where a clinician desires to have a clear reusable track to a target tissue for future treatment options. Embodiments also comprise structure and functionality configured to enable the ejection and deposition of therapeutic and/or diagnostic elements and/or substances in the open beak configuration for precise deposition thereof within the area of a biopsy site.

Figure 6:
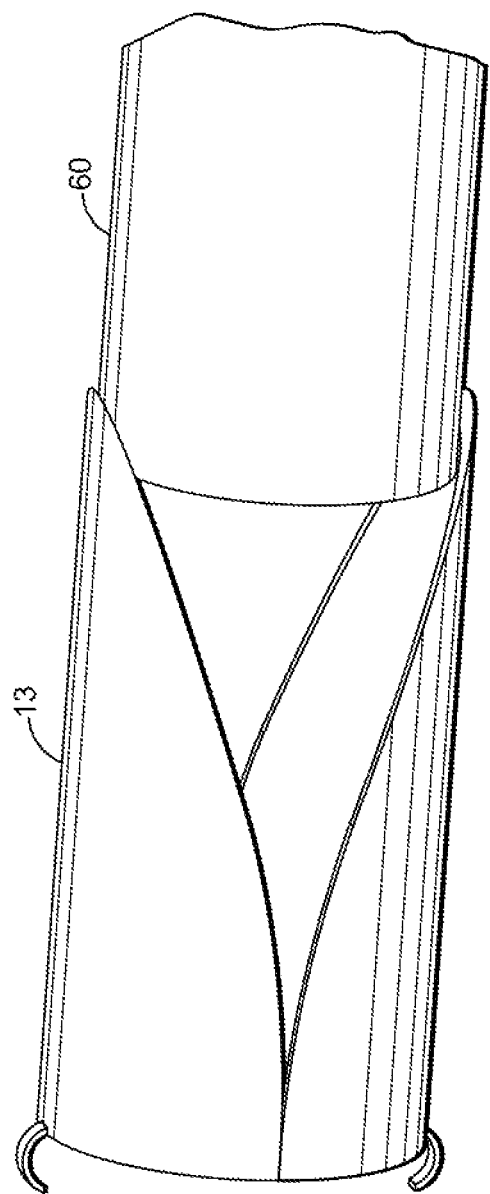
FIG. 6 shows the cutting, sharp cutting elements of a beak assembly engaging a core sample, according to one embodiment.

FIG. 6 shows the coring, sharp cutting elements of beak assembly 13 engaging a core sample 60. This figure also may represent the coring, sharp cutting elements of beak assembly 13 in the open position, delivering an in-situ marking element, by ejecting the marking element 60 via the coring and transport assembly 11 of the present biopsy device 10. Alternatively still, the element 60 may represent some other therapeutically-active element, such as a radioactive seed for brachytherapy, or a porous element loaded with a biologically active substance.

Figure 7:
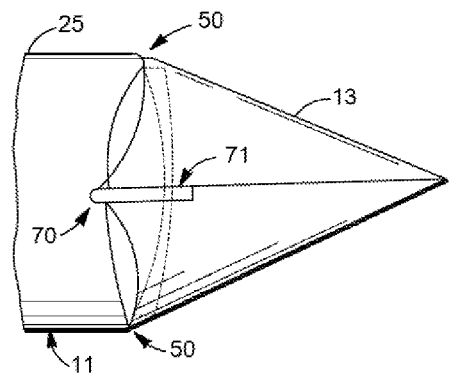
FIG. 7 is a side view of a beak of a core biopsy device according to one embodiment.
Figure 8:
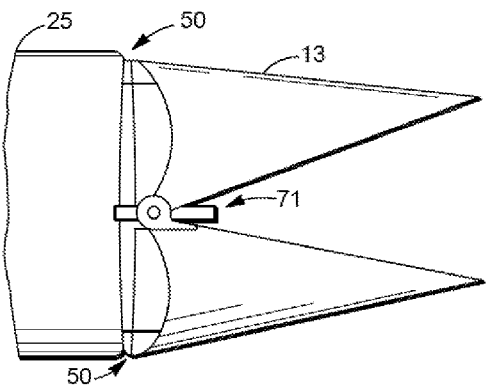
FIG. 8 is a side view of a beak of a core biopsy device according to one embodiment.
Figure 9:
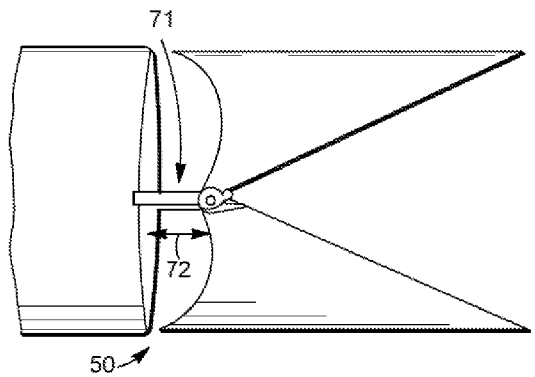
FIG. 9 is a side view of a beak of a core biopsy device according to one embodiment.
Figure 10:
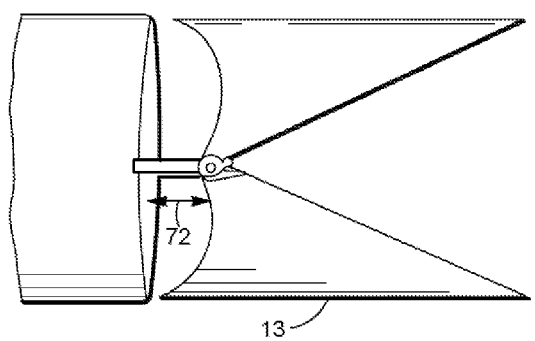
FIG. 10 is a side view of a beak of a core biopsy device according to one embodiment.
Figure 11:
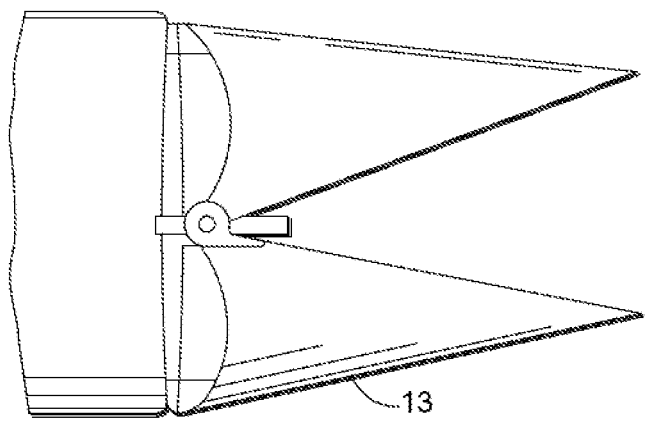
FIG. 11 is a side view of a beak of a core biopsy device according to one embodiment.
Figure 12:
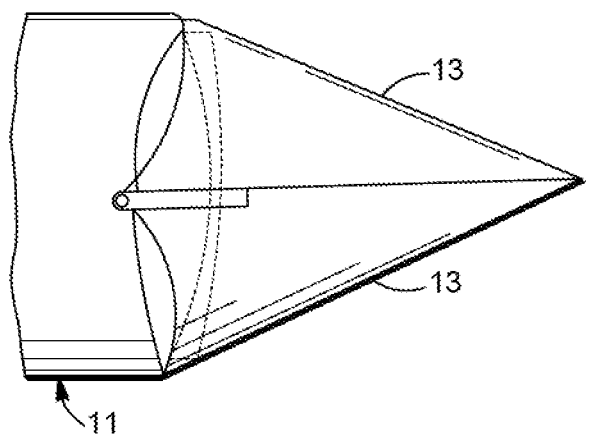
FIG. 12 is a side view of a beak of a core biopsy device according to one embodiment.

FIGS. 7-12 show a beak of the core biopsy device of FIG. 1 in various sequential stages ranging from closed to midway open to fully open coring and/or delivery positions, as well as next stages progressing from fully open to midway closed to fully closed part-off and/or closed penetration positions, according to embodiments. Indeed, FIGS. 7-12 illustrate various phases of operation and functionality of components of the coring biopsy device of FIG. 1, according to embodiments. Specifically, FIG. 7 illustrates a side view of the phase of rotation and forward or distal axial movement of the tubular coring and transport assembly 11 and attached cutting elements of beak assembly 13 in a closed configuration, as well as additional hinge assembly(ies) 70 connected to protruding element(s) 71 of an inner tubular element/helical element 26 of the tubular coring and transport assembly 11. FIG. 8 is a side view of partially opened, rotating and axially forward shifting, cutting elements of beak assembly 13 as they open to forward/spiral-outward core a tissue specimen (not shown) and/or to deliver materials (not shown) into the tissue. Illustrated in FIG. 8 are details of the interactions between the elements of the beak assembly 13, hinge assemblies 50, the non- or differentially rotating outer tubular element 25 of the tubular coring and transport assembly 11 as well as distally protruding elements 71 of an inner rotating tubular and/or helical delivery component 26 of the tubular coring and transport assembly 11, which serve to open the beak assembly 13 due to the changing plane of the hinge assemblies contacting the outer tubular element 25 with respect to the points contacting the protruding elements 71 of the inner component 26 of the tubular coring and transport assembly 11. FIG. 9 illustrates a widely open phase of the tubular coring and transport assembly 11 and the cutting beaks 13, further showing the changing planes 72 of the hinge assemblies 70 and 50 so as to actuate the cutting elements of beak assembly 13. It should be noted that rotation and axial movement of the cutting elements continue throughout these as well as the next illustrated phases, as shown in FIGS. 10, 11 and 12.

FIGS. 10, 11 and 12 show the phases of wide-open coring/delivery (FIG. 10), followed in sequence by spiraling, closing down movement of the beak assembly 13 during rotation and axial movement of these elements, as well as components of the tubular coring and transport assembly 11. FIG. 12 shows the position that leads to a complete severing of the core tissue specimen (not shown) from its base connection point with the host tissue, by the cutting, part-off beak elements 13 of the tubular coring and transport assembly 11, according to one embodiment.

Figure 13:
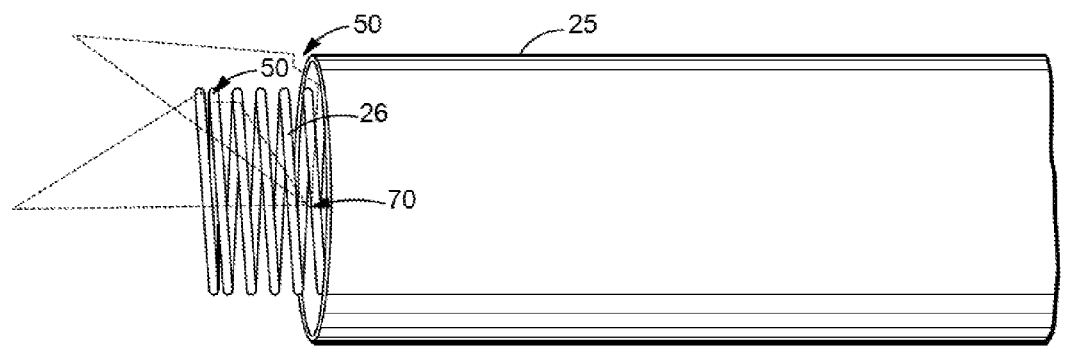
FIG. 13 is a side view of a penetration/coring/part-off/delivery beak of a core biopsy device in a closed, penetration or part-off position as well as a superimposed, open coring and/or delivery position with hinge assemblies as shown, according to one embodiment.
Figure 14:
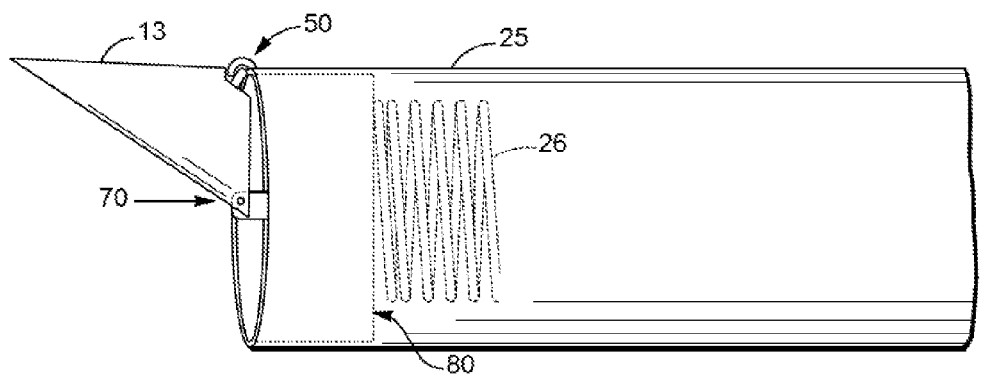
FIG. 14 is a side view of one beak element of a penetration/coring/part-off/delivery beak of a core biopsy device in an open coring and/or delivery position, according to one embodiment.
Figure 15:
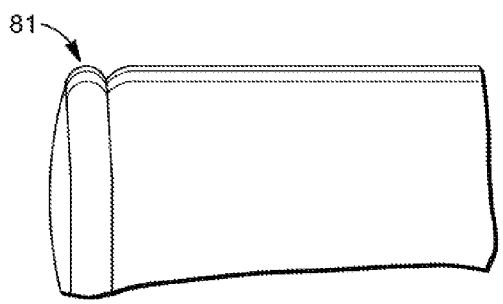
FIG. 15 is a side view of a non-rotating or differentially rotating outer tubular element of a core biopsy device and a section for interacting with a beak assembly (including, for example, elements 13), according to one embodiment.

FIGS. 13, 14 and 15 illustrate various hinge assembly alternative details for the interaction between the cutting elements of beak assembly 13 and the other components of the tubular coring and transport assembly 11, for the purposes of actuating the cutting elements of beak assembly 13, according to further embodiments. FIG. 13 shows an embodiment in which the hinge assembly or assemblies 50 are displaced inwardly during forward pivoting and movement, with respect to the hinge assemblies 70. In this embodiment, the rotating helical transport element 26 may be used to move the hinge assemblies 50 while an additional rotating inner component (not shown) placed in radial position between the outer non- or differentially rotating outer tubular element 25, may be used to anchor the hinge assemby(ies) 70. FIG. 14 shows another embodiment in which the hinge assembly(ies) 50 of the cutting beak assembly 13 are secured in plane by the outer, non- or differentially rotating outer tubular element 25, while hinge assemby(ies) 70 protrude distally to open then retract back proximally to close the cutting elements of beak assembly 13, which may be configured to rotate while moving outwardly, distal-axially to open, and which move inwardly to close down under rotational, axial motion. Such movements may be either directed distally and/or proximally, depending on the particular phase of the entire cycle of operation of the present biopsy device. Advantageously, locating hinge assemblies 50 as shown in FIG. 14 enables the outer diameter of the cutting elements of beak assembly 13 to be precisely controllable and reliably located. Such hinge assemblies 50 enable the cutting elements of beak assembly 13 to not exceed (any more than is desirable), the outer diameter of the more proximal coring/transport outer tubular element 25. Yet, the cutting elements of beak assembly 13 may be configured to enable them to hinge sufficiently inward to occlude and part-off/sever the core sample at the end of each coring cycle. FIG. 14 also shows an embodiment that comprises an inner helical transport coring element 26 of a tubular coring and transport assembly 11 within the outer non- or differentially rotating outer tubular element 25 of the tubular coring and transport assembly 11. This helical element 26 may be configured to terminate in a collar section 80 which may attach to (a) protruding element(s) 71 that serve(s) as anchoring hinge assemblies 70 for rotating, cutting beak assembly 13 of the biopsy device of FIG. 1. The differential movement of the planes of hinge assemblies 70 with respect to hinge assemblies 50 results in opening and closing of cutting beak assembly 13, in correct precise timing such that the functions called for in each stage of the coring/biopsy cycle are fulfilled.

FIG. 15 shows details such as examples of flaring, tapering surfaces 81 of an outer non- or differentially rotating outer tubular element 25 of the tubular coring and transport assembly 11, which may serve as a locating rim 81 with which to actuate hinge assembly(ies) 50 of the cutting beak assembly 13, as outer tubular element 25 and hinge assembly 50 move together axially relative to hinge assembly(ies) 70.

Figure 16:
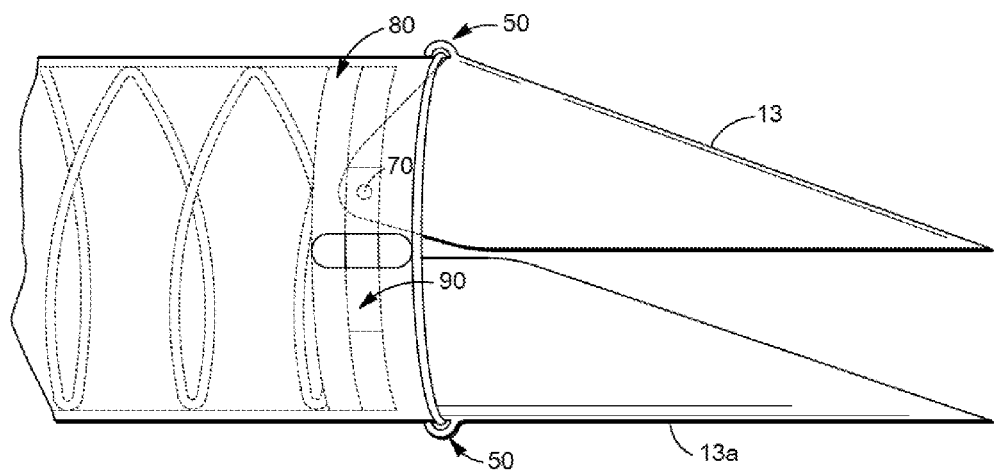
FIG. 16 is a side view of a penetration/coring/part-off/delivery beak assembly of a core biopsy device of FIG. 1 with one beak element in a closed, penetration or part-off position, with its inner element shown in dash lines, and another beak element in an open coring and/or delivery position with its inner element hidden by an outer sheath tube, and hinge assembly, according to one embodiment.

FIG. 16 shows one embodiment including one cutting beak element 13 in a closed position, while an additional cutting beak element 13a is shown in wide-open position to illustrate the relative positions of the hinge assemblies 50 and 70. In this representation, further details of hinge assembly(ies) 70 are shown, with axial and radial positions constrained sufficiently by a slot element 90 or some other configuration such as a trough configuration, within an inner forward collar section 80 of a helical coring/transport element 26 of the tubular coring and transport assembly 11. These elements together act to rotate the beak assembly 13 and also to move the hinge assemblies 70 in an axial direction distally and proximally relative to hinge assembly(ies) 50 to actuate opening and closing of the cutting beak assembly 13 in the various phases illustrated previously.

Figure 17:
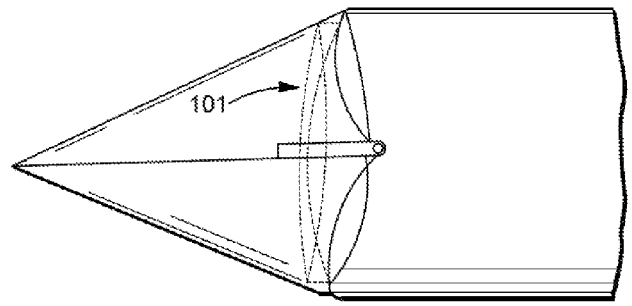
FIG. 17 is a side view of a beak assembly of a core biopsy device in a first closed configuration, with an additional coring/transport/supporting element, according to one embodiment.
Figure 18:
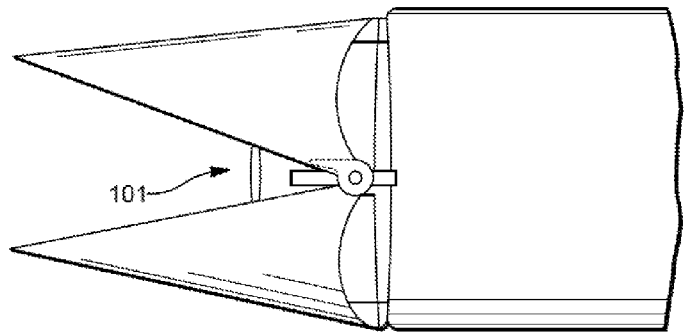
FIG. 18 is a side view of a beak assembly of a core biopsy device in a second midway open configuration, with an additional coring/transport/supporting element, according to one embodiment.
Figure 19:
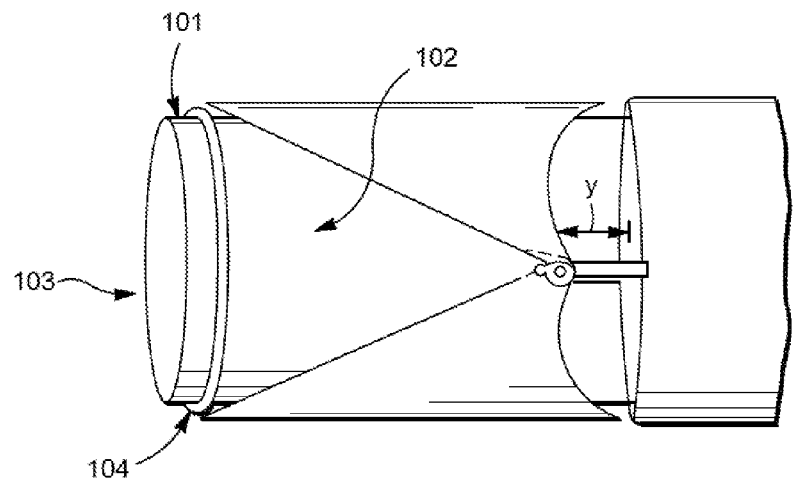
FIG. 19 is a side view of a beak assembly of a core biopsy device in a third open to coring and/or delivery positions, with an additional coring/transport/supporting element, according to one embodiment.

FIGS. 17, 18 and 19 show a configuration with a forward cutting edge of an additional cutting, tubular component 101 of an inner coring/transport helical tubular transport assembly 102, according to still further embodiments. In this case, the cutting beak assembly 13 actions may be supported and augmented by this additional cutting transport assembly 102. In this configuration, the cutting beaks 13 may be supported more firmly at their distal points and may be aided in coring by an additional forward-edge-sharpened surface 103 (distal edge), rotating and distally-moving component 101. In this illustration, a bearing surface rim 104 may be provided to protect the side edges of the rotating, cutting beak assembly 13.

Figure 20:
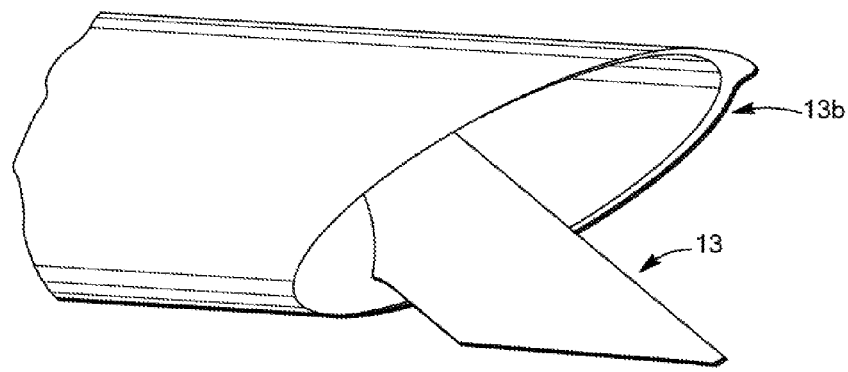
FIG. 20 is a side perspective view of a beaks assembly of a core biopsy device according to one embodiment.
Figure 21:
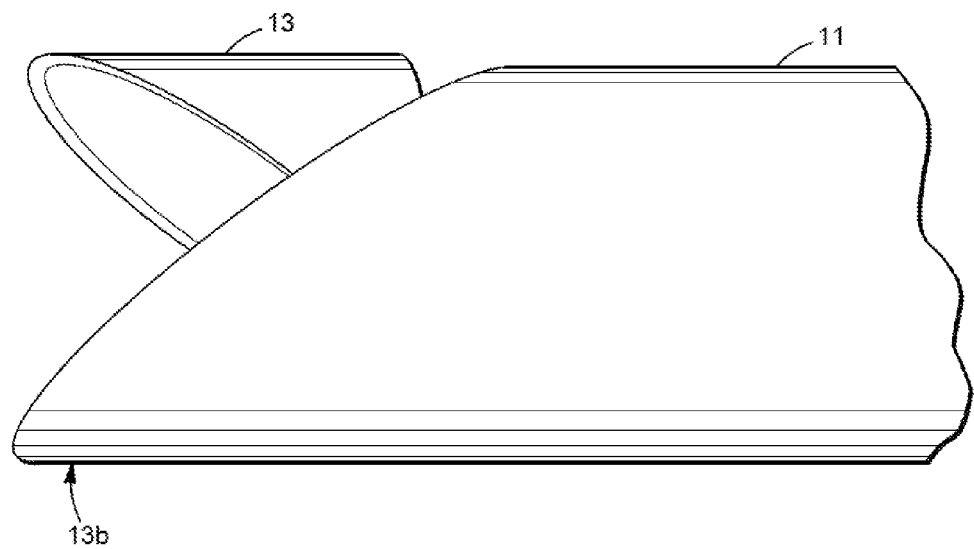
FIG. 21 is a side perspective view of a beaks assembly of a core biopsy device according to one embodiment.
Figure 22:
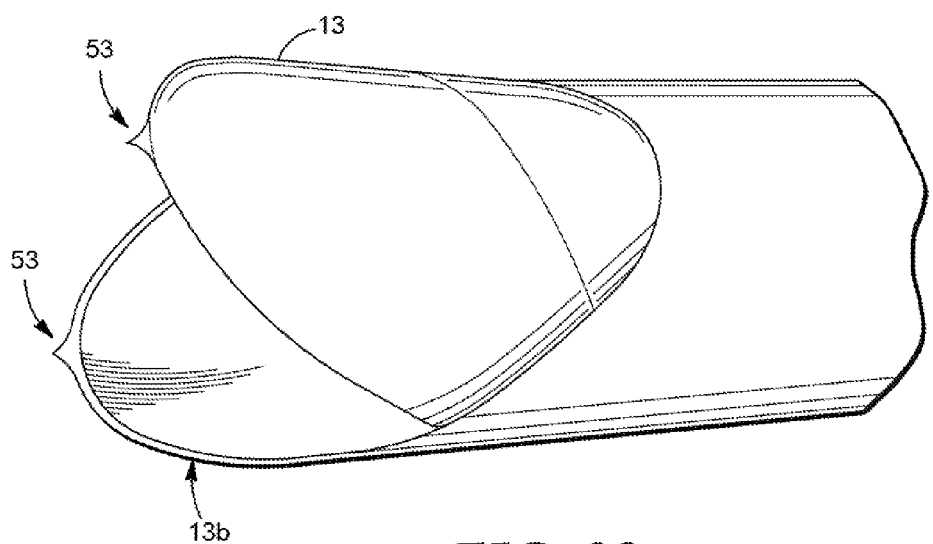
FIG. 22 is a side perspective view of a beaks assembly of a core biopsy device according to one embodiment.
Figure 23A:
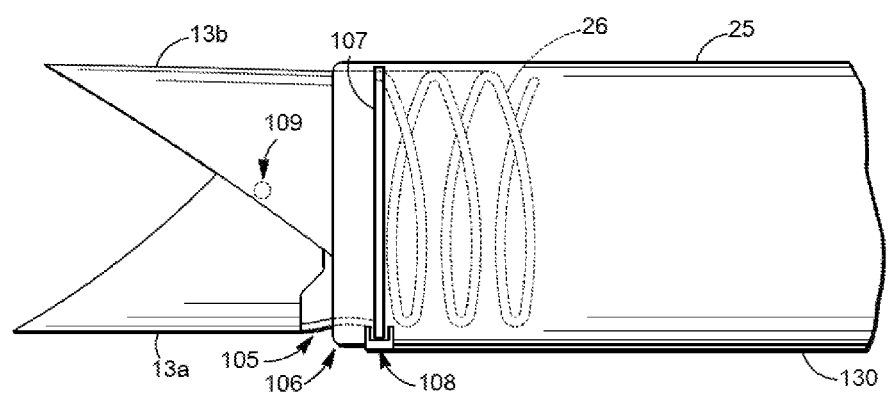
FIG. 23a is a side view of fixed and hinged beaks of a beak assembly according to one embodiment, in an open configuration, along with opening and closing actuating components, as well as hinge and pivot points.
Figure 23B:
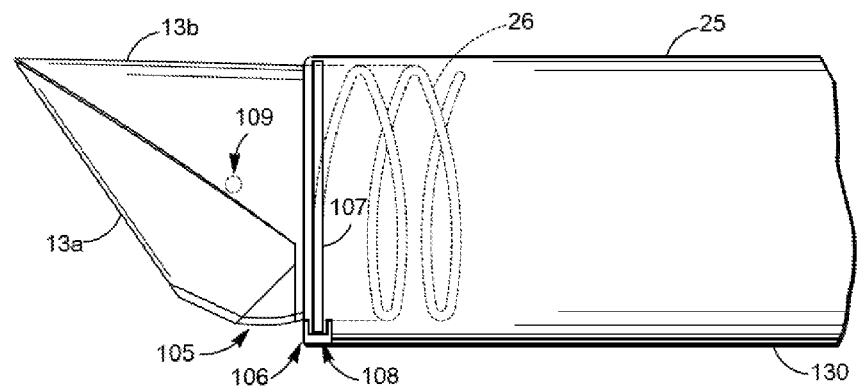
FIG. 23b is a side view of fixed and hinged beaks of a beak assembly according to one embodiment, in a closed configuration, along with opening and closing actuating components, as well as hinge and pivot points.

FIGS. 20, 21 and 22 show in various perspective views, an alternate configuration with a single, hinged, rotating, cutting beak element 13, with an opposite fixed (non-hinged), rotating, cutting beak element 13b, according to still another embodiment. FIGS. 23a and 23b are side views of the single hinged rotating cutting beak 13a and the fixed hinge rotating cutting beak 13b shown in FIGS. 20-22. According to one embodiment, the hinged cutting beak 13a is shown fitted with a slide locator hinge tab 105 at hinge assembly 106 (similar in location to hinge assembly 50 FIG. 14). The purpose of this slide locator hinge tab 105 is to rotate inside core/transport outer tubular element 25 along with inner helical core/transporting component 26, yet enable axial movement so as to close cutting beak element 13b inwards towards cutting beak 13a for the purposes of closed beak penetration, and parting off or severing a core sample at its base attachment point at the end of the coring stage. As shown, the axially actuating slide locator hinge tab 105 causes actuator rod 130 to interact with slide ridge/rim 107, which may be connected to slide locator hinge tab 105. As actuating rod 130 moves distally and proximally in an axial direction, its force may be transmitted via clevis 108, through slot in outer tubular element 25, to the ridge/rim 107 which, in turn, moves slide locator hinge tab 105 a corresponding distance and direction. This action moves rotating beak 13b about its other hinge pivots 109 on non-hinged rotating beak 13a, to oppose (close down upon) rotating beak 13a along its sides and front cutting edges for the purposes of closing the end of coring and transport assembly 11 for penetration and/or parting off of a core sample at its base connection with host tissue. Also, beak tips 53 may be configured to work together in cutting action by resting in closed position adjacent to each other (scissors action when rotating), to meet at their tips only, or to assume an "overbite", "underbite" or other configuration to assure positive part off of the tissue specimen to be collected for transport, regardless of whether other adjacent beak edges completely touch along their entire border or not.

Figure 24:
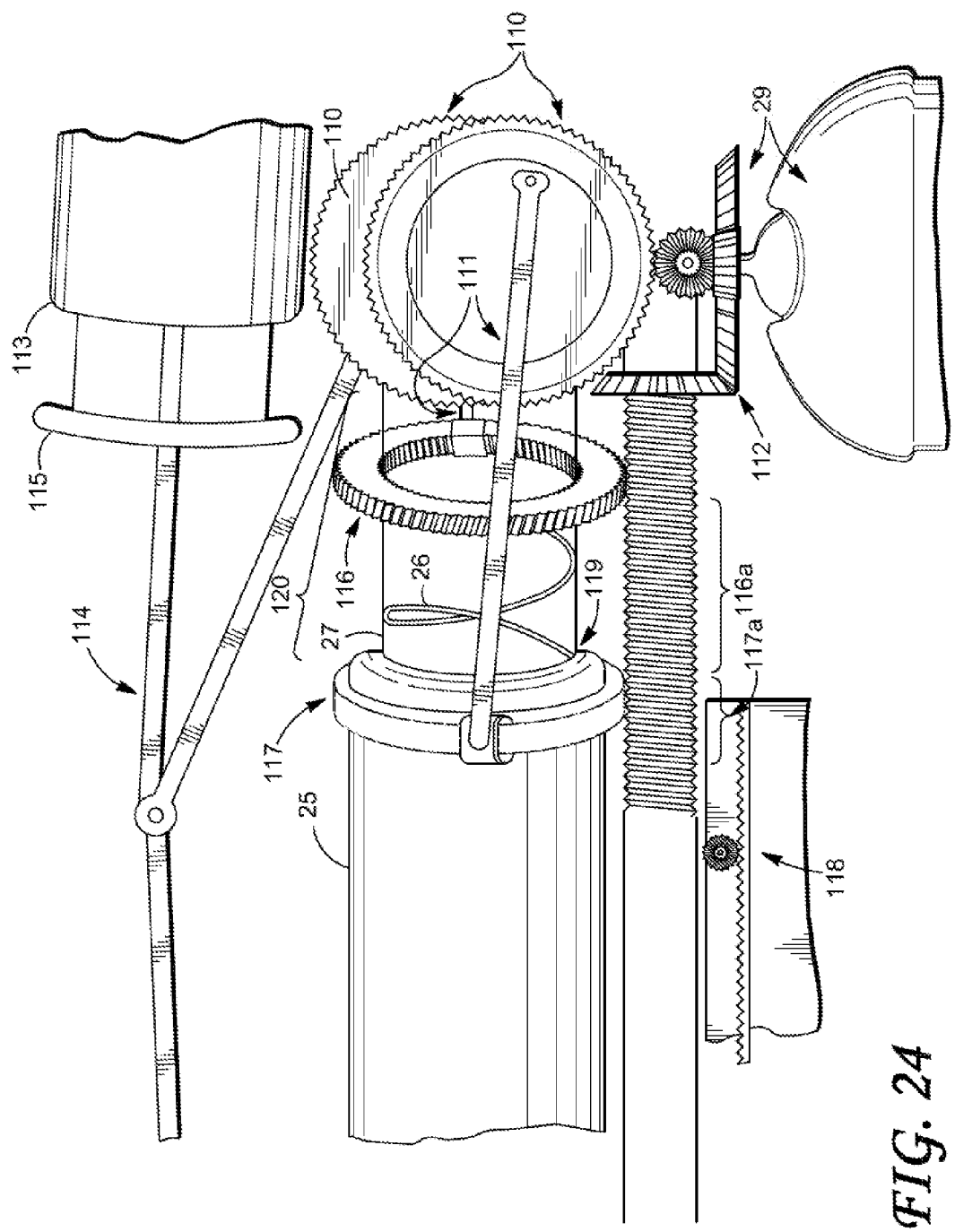
FIG. 24 is a close up side view of a driving mechanism for components of beak actuation elements of a biopsy device, as well as a driving mechanism for a vacuum assisting element and a rack-and-pinion rack element of the present biopsy device, in addition to a motor drive element of the present biopsy device, according to one embodiment.
Figure 39:
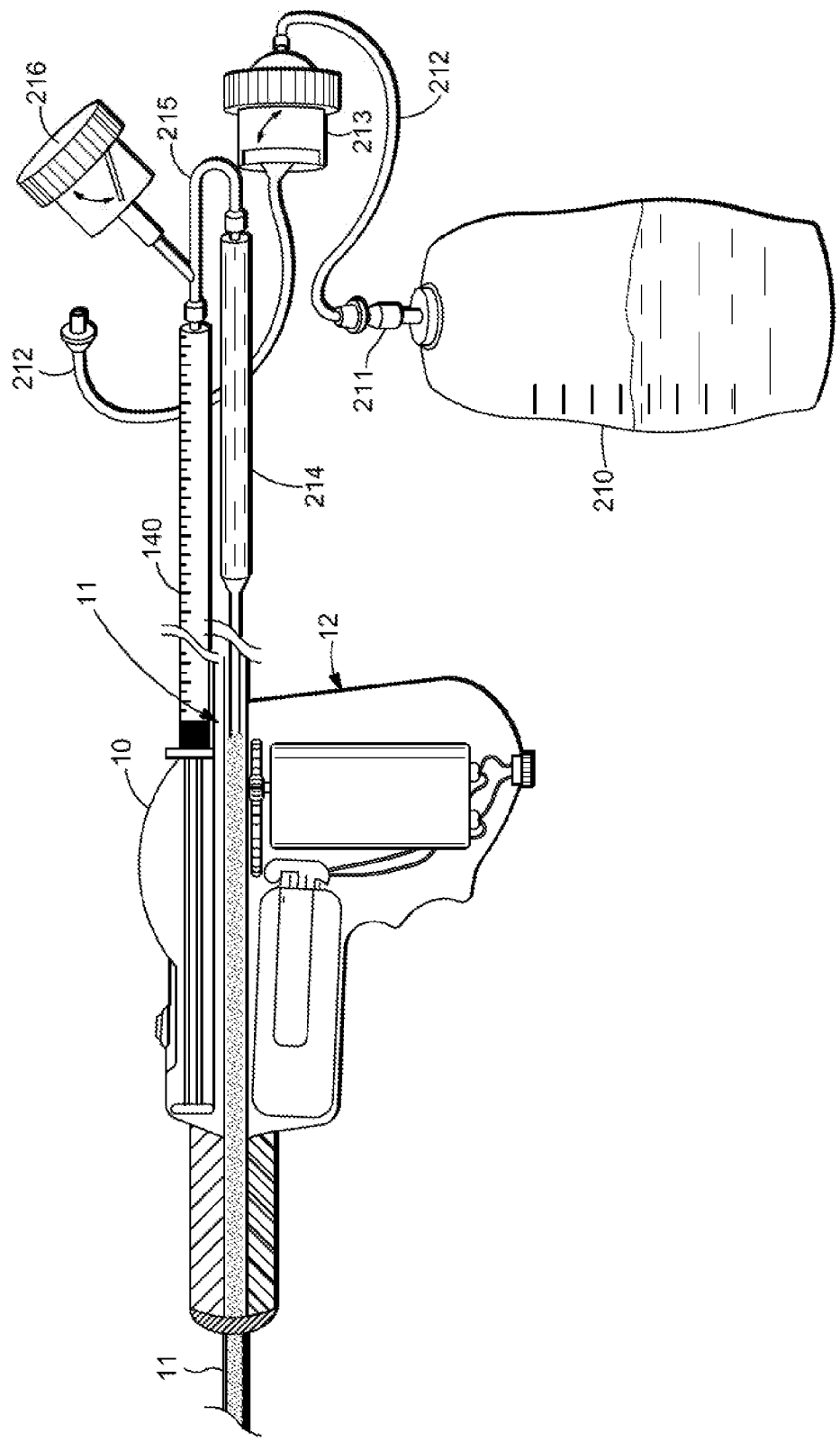
FIG. 39 is a side view of a biopsy device, showing a vacuum/delivery assembly 140 of FIG. 31, a connecting tube and valvular assembly, as well as an additional connecting tube and in-line valve component, in addition to a collection receptacle, according to one embodiment.

Referring now to the mechanisms of actuation of the rotating, cutting beaks, FIG. 24 shows a driving motor/clutch assembly 29, a set of gear and crank/connecting rod assemblies 110, 111, as well as their relationships with outer tubular element 25 and transport elements 26 (helix) and 27 (magazine) of tubular coring and transport assembly 11, according to one embodiment. These assemblies may be configured to sequentially and continuously actuate the outer tubular element 25 and transport element 26 in rotation and axial movements. As shown in FIG. 24, a large gear and connecting rod assembly 110 and 111 related to and acting on an inner non- or differentially rotating helical tubular component 26 via a slide/ring/and/or gear component 116 may be provided, as well as a similar assembly 110 and 111 related to and acting on a non- or differentially rotating outer tubular element 25 via a similar slide/ring or gear assembly 117. In one embodiment, the gear and connecting rod crank-type assemblies 110 and 111 may be configured to move the outer tubular element 25 and transport element 26, themselves components of the tubular coring and transport assembly 11, relative to one another such that, in turn, the outer tubular elements 25 and transport element 26 individually act on the cutting beak assembly 13, FIG. 1, along the long axis of the biopsy device 10, to cause the cutting beak assembly 13 to open and close while rotating so that they may be able to open widely within the tissue for coring and then at the end of the coring cycle close back down against one another to sever the base attachment of the core sample. For illustration purposes, it is useful to refer once again to the individual components as shown in FIG. 14, including tubular non- or differentially rotating outer tubular element 25, inner helical non- or differentially rotating coring/transport element 26 as well as cutting beak assembly 13. As is further shown in FIG. 24, the driving motor/clutch assembly 29 may be coupled, via gearing assemblies 112, to one or both of the outer tubular elements 25 and transport element 26, such as by a worm gear and bevel gear set as shown or by some other functionally equivalent assembly or assemblies, thus achieving matched or differential speeds of both rotation and beak penetration/opening/closing, as desired. The purpose of such a mechanism as shown in this embodiment of FIG. 24, and also referring to the elements 25, 26 and 13 in FIG. 14, may be to rotate one or both of the outer tubular elements 25 and transport element 26, in either the same or opposite directions, which then also rotate the cutting beak assembly 13 during the various phases of coring, part-off/sever the core sample (not shown) and transport the same back proximally through the handle 12, via the tubular coring and transport assembly 11, outer tubular element 25 and transport element 26 and/or magazine element 27 at the junction 119 of elements 26 and 27 of the biopsy device 10 and into a storage magazine 27 such as shown in FIG. 3. The worm gear element of gear assembly 112 may be divided into two sections with different pitch (not shown), for instance a pitch associated with slide/ring component 116 (116a) and a relatively different pitch for slide/ring/or gear component 117, itself gear pitch matched to its corresponding section 117a of the worm gear. Such an arrangement would provide one means of differentially rotating outer element 25 relative to the rotational speed of inner element 26. A further illustration shown in FIG. 24 refers to a vacuum/delivery mechanism (also designated element 140, FIG. 30 described below), which may comprise a syringe type component 113 and associated crank/connecting rod attachments 114 to one or more gears or other mechanisms (not shown) to drive a plunger assembly 115 back and forth to create positive pressure and/or vacuum, which may aid in coring and transport. The vacuum/delivery component 113 may be coupled via, for example, tube and valve assemblies (not shown) to a storage magazine 27 such as shown in FIG. 2 for the purposes of augmenting core specimen movement into a storage magazine 27, such as shown in FIG. 2. Additionally, a vacuum/delivery component may also be used to deliver components (not shown) to the biopsy site via the tubular coring and transport assembly 11. A vacuum/delivery component may also be used to draw fluids and loose tissue cells from the target site (lesion or other site) for collection and later cytologic analysis, such as shown in FIG. 39, as discussed below.

Lastly in FIG. 24, a rack-and-pinion assembly may be provided, as shown at reference numeral 118 in FIG. 24. This rack-and-pinion mechanism may be configured to move, as a unit, a carriage or sub-stage structure (not shown here) back and forth (distally and/or proximally) within and relative to handle 12. This internal (to handle 12 of FIG. 1) sub-structure may contain as a unit, the assembly of components including driving motor assembly 29, as well as gearing assemblies 112, tubular elements 25 and transport element 26 of the tubular coring and transport assembly 11 as well as the attached cutting beak assembly 13, and in one embodiment, vacuum/delivery components 113 and 114 and tissue specimen storage magazine element(s) 27. An effect of such movement would be to shorten or lengthen, such as distances 116a, 117a (not proportional to actual) the axial excursion of the coring components of biopsy device 10, during the coring/part-off phases, thus shortening or lengthening the core sample obtained, which in turn may lead to higher correlation of sequential samples taken with the video imaging of the procedure as well as the written record of sequential samples taken from the site. This mechanism may itself also be used as a simple, repetitive penetration mode function of this device, where the operator desires to penetrate the tissue in either closed or open beak configuration, with or without rotation, and in short stages. Such use would allow for slow or deliberate, precisely staged tissue penetration to a target tissue site, for instance when the device is rigidly locked to a stereotactic table. This mechanism may be powered by any means, including but not limited to, user controlled electrical power, mechanical, or manual (operator power such as a finger/thumb slide lever). If powered electrically, provision for selectable excursion may be provided (mechanism not shown). Also shown in FIG. 24 is the telescoping relationships at 119 between internal helical coring/transport element 26 and outer tubular element 25, as well as with a section of a storage magazine 27 (distal section of storage magazine 27 slid over element 26 and entering element 25 represented by area 120). This arrangement may be configured to provide a vacuum-tight connection all along area 120 so that vacuum and/or delivery may be accomplished by vacuum/delivery components such as components 113 and 114.

Figure 25:
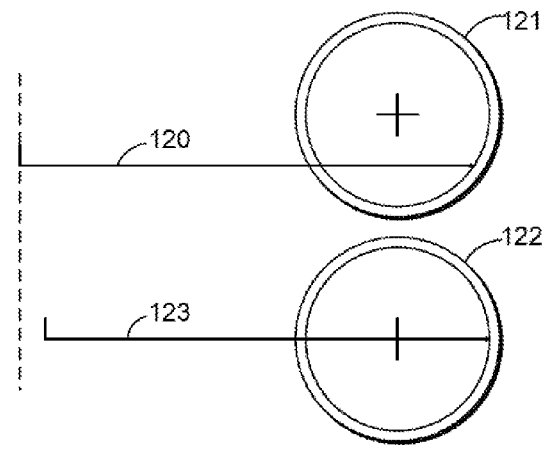
FIG. 25 is a side view of phases of drive element relationships used to actuate beak elements of a biopsy device, according to one embodiment.
Figure 26:
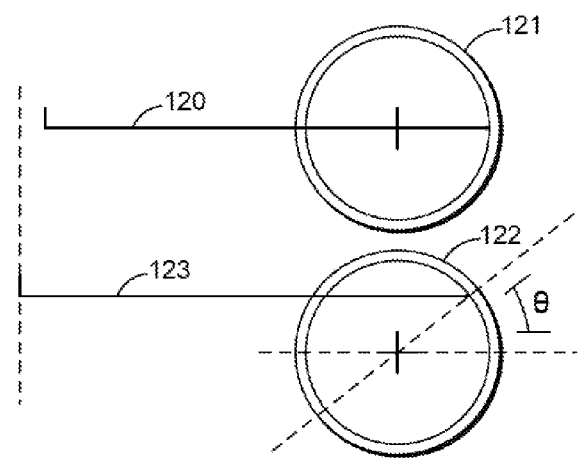
FIG. 26 is a side view of phases of drive element relationships used to actuate beak elements of a present biopsy device, according to one embodiment.
Figure 27:
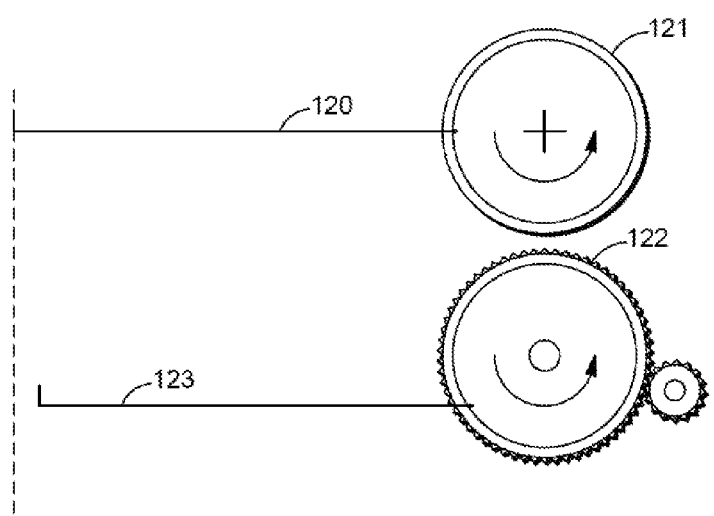
FIG. 27 is a side view of phases of drive element relationships used to actuate beak elements of the present biopsy device, according to one embodiment.

FIGS. 25, 26 and 27 illustrate stages of continuous movement of the present biopsy device 10, through stages of a coring biopsy sequence or coring phase of an entire biopsy procedure, according to further embodiments. These continuous movements may, however, be interrupted by an operator such that biopsy device 10 pauses in one stage or another as desired by the operator. Reasons for interruption may comprise prolonging a closed-beak configuration for purposes of penetration through difficult tissue, such as may occur in more fibrous breast tissue 16 and/or target lesion 15 of FIG. 2, or in order to pursue continuing to collect the sample but at a different angle, or to collect a longer specimen than originally envisioned at the start of the cycle. Gears and connecting rods such as 110 and 111 of FIG. 24 may be configured to act sequentially and in continuous and/or interrupted fashion, upon coring/transport tube elements 25 and transport element 26 (as illustrated in FIG. 16) individually such that axial movements of components such as 25 and transport element 26 of FIG. 16 will move cutting beak assembly 13 to open and close at the right moments to accomplish the various coring/part-off and other stages.

FIG. 25 shows one such stage (stage 1), appropriate for closed beak penetration through the tissue of an organ such as breast tissue 16 on the approach to a target lesion 15, as shown in FIG. 2. FIG. 25, for illustration purposes, splits the gears and connecting rods such as 110 and 111 of FIG. 24 into individual components, labeled as 121 and 122 for gears 110 of FIG. 24 and connecting rods 120 and 123 for connecting rods 111 of FIG. 24 As further illustrated in FIG. 25, connecting rod 120 may be driven by gear 121. Connecting rod 120 may be coupled, such as by a slide/ring/gear assembly 117 FIG. 24, to tubular element 25 of FIG. 24.

Element 122 may be a gear or disc, for example. In either case, gear 122 may be similar to and may be coupled to gear 121, such as by a single axle (not shown) coupled to both gear 121 and gear 122. Gear 122 may have a connecting rod 123 coupled thereto, which may also be similar to connecting rod 120. However, connecting rod 123 may be coupled by a slide ring mechanism 116 to inner helical tubular element 26 of FIG. 24. For purposes of illustration of one embodiment of this device, either connecting rod 120 or 123 of FIG. 25 may be further connected to rod 130 of FIG. 23a, 23b or 28, as suggested by the extension of a connecting rod from gear element 110 (not labeled) to actuator rod 114 in FIG. 24, which actuates the vacuum assembly plunger 115, with an extension distally (not labeled) along the outer element 25 of FIG. 24 to eventually become rod 130 of FIG. 28 in one embodiment of this device.

As noted, gears 121 and 122 may be solidly coupled together (as though superposed one over the other). However, the radial positions along gears 121 and 122 respectively, of connecting rods 120 and 123 may be purposely located differently such that a lead-lag relationship results between the positions of connecting rods 120 and 123 as gears 121 and 122 rotate in solid connection with one another. FIG. 25 shows the relationship between connecting rods 120 and 123 that results in closed beak assembly 13 configuration as a result of the attachments of connecting rods 120 and 121 respectively with tubular elements 25 and transport element 26 of FIG. 24, which may be coupled to cutting beak assembly 13 such as shown in FIG. 5. In this stage, connecting rod 120 associated with gear 121, lagging behind connecting rod 123 around gear 122 (assuming counter-clockwise rotation of both gears for illustration purposes), may be placed more distally with respect to handle 12 and with respect to connecting rod 123. This relationship results in cutting beak assembly 13 assuming a closed position. The stage shown in FIG. 25 would be useful for parting off or severing of the core sample at its base and would also be a useful stage, if interrupted, for closed beak assembly 13 rotation of tubular coring and transport assembly 11 and penetration by biopsy device 10 through breast tissue 16 on the approach to a target lesion 15, as shown in FIG. 2.

FIG. 26 shows a stage (stage 2) that is next in sequence relative to the stage shown in FIG. 25. This stage begins as connecting rod 123, moving around gear 122, positions itself more distally with respect to connecting rod 120. This relationship results in the cutting beak assembly 13 opening to a wide-open configuration, which may be advantageous for coring and/or delivery of, for example, markers or therapeutic agents to the site. It should be noted that both connecting rods 120 and 123 advance distally during this stage. However, since connecting rod 120 lags behind connecting rod 123, connecting rod 120 is more proximally placed than connecting rod 123 throughout this stage.

FIG. 27 shows the next stage in sequence (stage 3), where, as connecting rod 120 reaches its most distal position, connecting rod 123 has already moved back proximally on its journey towards its position in stage 1. The result of the more proximal position of connecting rod 123 with respect to connecting rod 120 results in cutting beak assembly 13 closing and remaining closed until connecting rods 120 and 123 change their relative positions with one another as they approach stage 1 once again (shown in FIG. 25). It is understood that the shapes of discs, which may act on connecting rods 120 and 123, attached to gears 121 and 122 (gears may be round, however, discs attaching to the connecting rods 120 and 123 may be of other shapes), be other than circular, such as elliptically shaped (not shown), so as to vary the time spent in the various stages and relationships between connecting rods 120 and 123.

Figure 28:
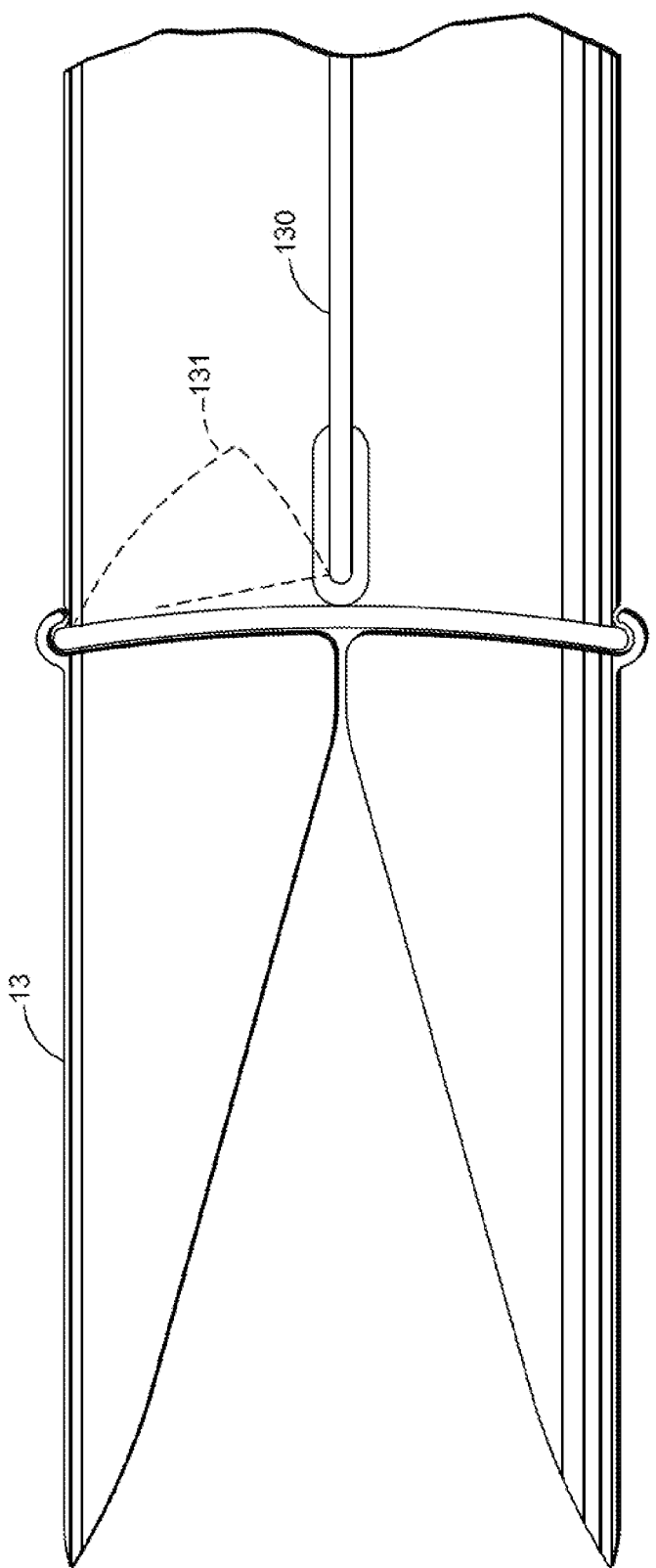
FIG. 28 is a side view of a non-rotating or differentially rotating outer tubular element of a core biopsy device and a section interacting with (a) beak assembly of FIG. 14, as well as supplemental actuation augmenting rod element(s) of the present biopsy device, according to one embodiment.
Figure 29:
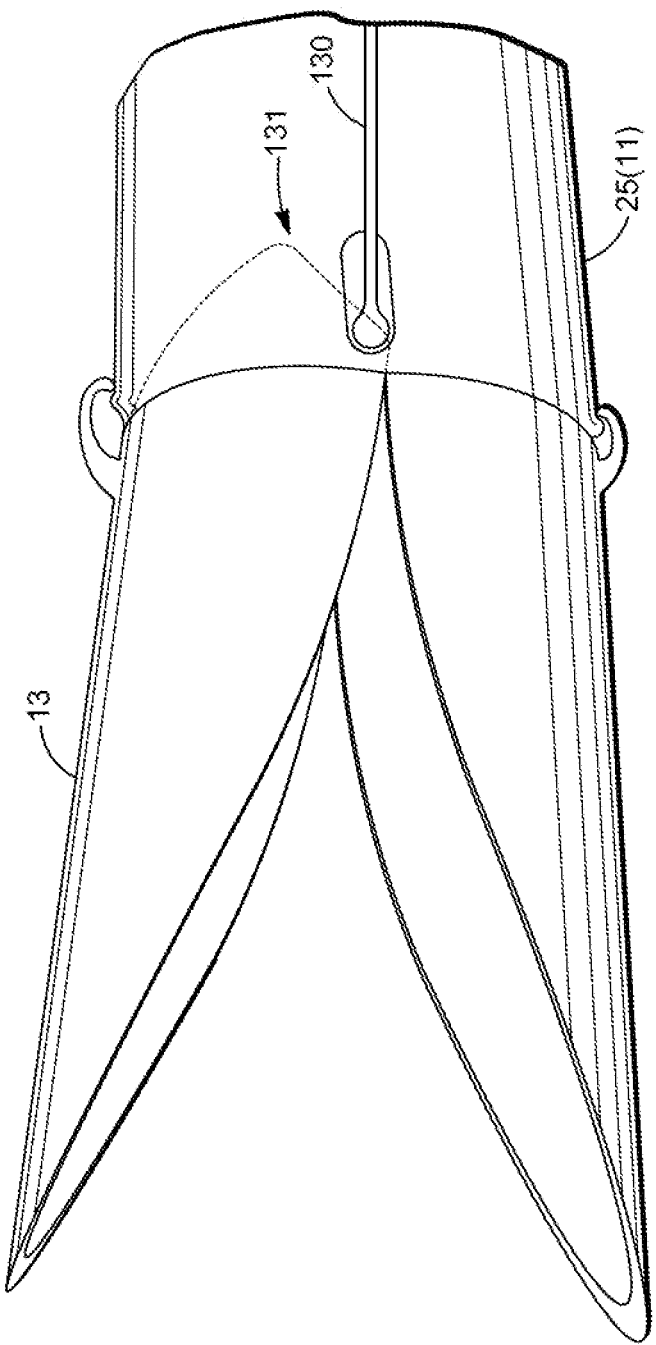
FIG. 29 is a side-perspective view of a non-rotating or differentially rotating outer tubular element of a core biopsy device and a section interacting with a beak assembly, as well as supplemental actuation augmenting rod element(s) of present biopsy device, according to one embodiment.
Figure 30:
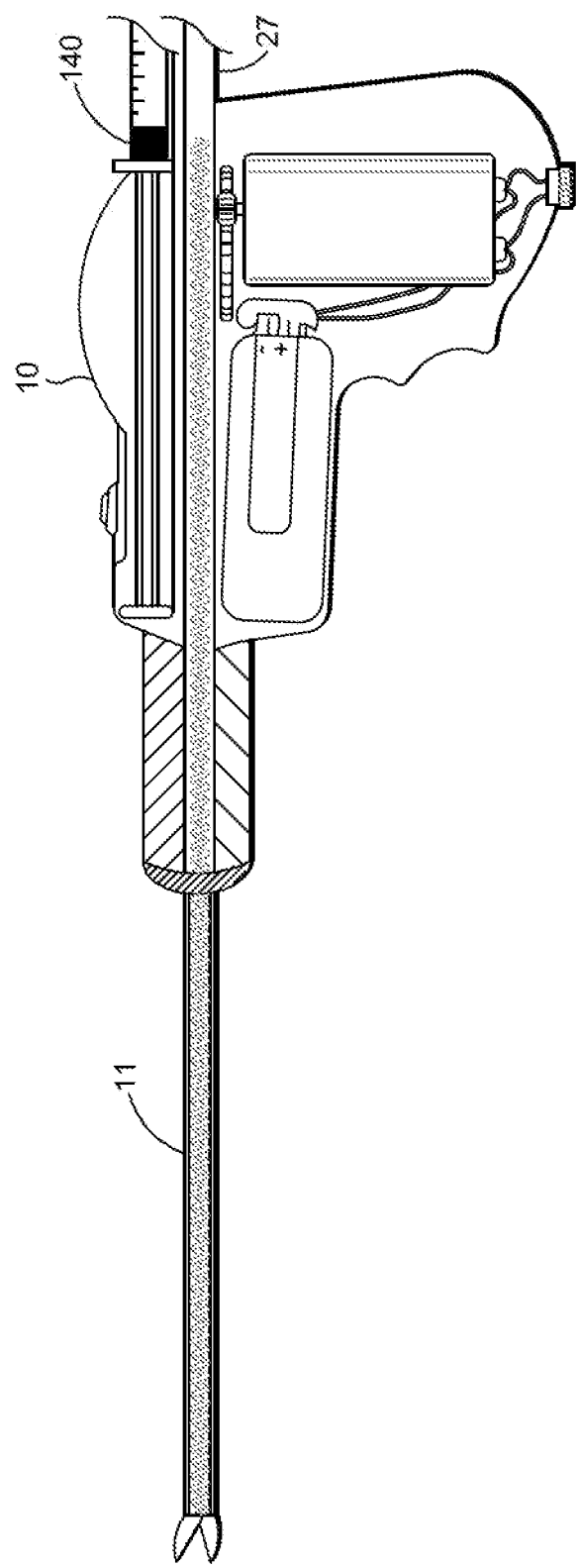
FIG. 30 is a side view of a core biopsy device showing internal components including a transport helical element, power supply, motor drive unit, augmenting vacuum elements and an external power supply plug in socket, as well as an on/off switch element, according to one embodiment.

FIG. 28 shows a side view comprising an additional rod element(s) 130 designed to act upon the same hinge assembly area(s) 70 (FIG. 7), as acted upon by the inner helical coring/transport element 26 of FIG. 24, according to one embodiment. The rod element 130 may be configured to strengthen (augment) or replace the axial action upon the cutting beak assembly 13 of the inner helical coring/transport element 26 of FIG. 24 or rod 120 of FIG. 25, since the precision available from a solid rod such as element 130 may be more robust and exact compared with that available with a helical component such as component 26 of FIG. 24. According to such an embodiment, rod element 130 may be actuated in a manner and through a mechanism that may be similar to that shown acting on inner helical coring/transport element 26 of FIG. 24, for the purposes of moving the hinge assembly(ies) 70 of FIG. 7, of cutting beak assembly 13 of the present FIG. 28. FIG. 28 also shows by dotted lines a most proximal position of a proximal portion 131 of cutting beak assembly 13 in closed position. Rod element(s) 130 may control cutting beak assembly axial motions via a similar slide/ring arrangement (not shown in FIG. 28) as shown inside the handle such as slide/ring elements 116 and 117. FIG. 24. FIG. 29 is a perspective view showing the same elements, including rod element 130, as shown in FIG. 28. Also, it is to be understood that if these control rods are outside the inner helical element, but inside the outer tubular element, that the action of rotating the helical element with tissue sliding along the rods, which rotate with the outer tubular element at a different speed or direction, may assist in transport of the tissue specimen obtained. It is also possible, if the outer tubular element is of a different cross sectional shape than a circle, and for instance is a square, that the control rods could nest in the inner corners along the length of the outer tubular element. FIG. 30 is a side view of biopsy device 10, according to one embodiment. Attention is directed to vacuum augmentation assembly 140 in parallel with coring/transport components 11 of FIG. 1 and FIG. 2 to illustrate that simultaneous movement of the vacuum/delivery assembly 140 with those of components 11 may result in augmentation of coring and transportation of biopsy specimens (not shown) into and within storage magazine 27.

Figure 31:
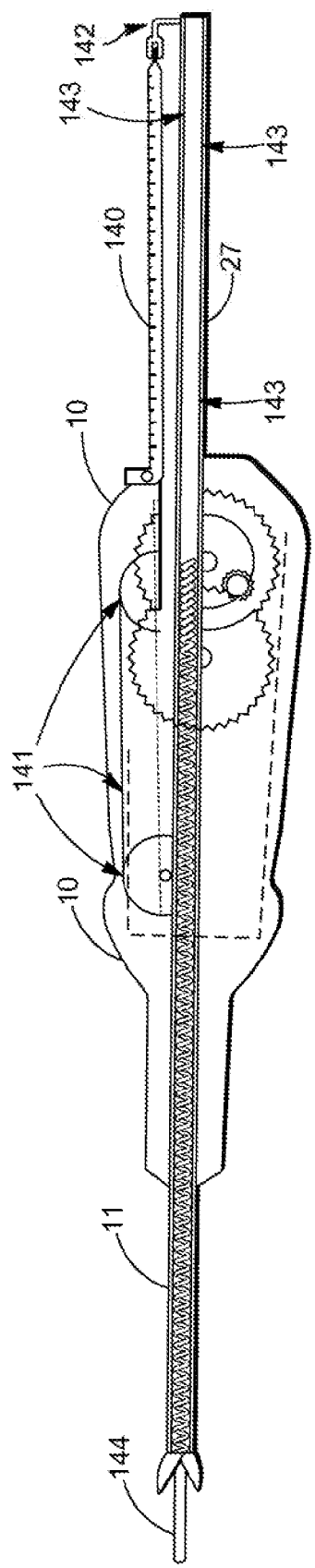
FIG. 31 is a top view of a core biopsy device, showing internal components including a transport helical element, drive gears for actuating beak elements as well as a pulley and belt system and elements of a storage tube magazine with fenestration elements, as well as a movable guiding element, according to one embodiment.

FIG. 31 is a top view, according to embodiments, of the biopsy device 10 of FIG. 30 showing a belt pulley mechanism 141 for driving vacuum/delivery assembly 140 such that continuous cycling of vacuum/transport components is possible during activation of these components. FIG. 31 also shows additional structures of connection(s) 142 between vacuum/delivery assembly 140 and a storage magazine 27. Storage magazine 27 may have an internal helical transport component (not shown) similar to and extending from the component 26 of FIG. 24 of the tubular coring and transport assembly 11 of FIG. 2. Storage magazine 27 may also have fenestrations or openings 143 along its length, each of optionally varying and/or progressively varying dimensions for the purposes of evenly and/or progressively distributing vacuum and/or positive pressure for material handling of tissue specimens (not shown), such as for sequentially collecting and/or emptying tissue samples (not shown), and/or for delivery/deposit inside organs such as breast tissue 16 of certain materials (not shown) such as marker implants; tracer elements; medications for pre-treatments, intra-procedure treatments and/or post-treatments; and the like. FIG. 31 also shows a partial segment of an optional guiding element 144, such as a movable or fixed guiding wire or needle, which may temporarily occupy a longitudinal lumen (such as along the inside of the helical coring/transport element 26) in device 10, or may be placed adjacent to the central core of biopsy device 10 such as in a barrel and/or loop or series of loops positioned along a line parallel to the central core of biopsy device 10 (this position not shown). The guiding element 144 may comprise, for example, a laser light directed along the path of the tubular coring and transport assembly 11 of the biopsy device 10 or other visual guiding aid, rather than (or in addition to) a solid material such as a needle or wire. If the tubular coring and transport element is configured to be bendable, it could follow over such a needle or wire that may be rigidly curved, for example, and prepositioned to follow a prescribed path to the target tissue. Element 144 may also be a simple hollow tube (rather than a needle with a sharp tip), which tube may be stiff, flexible, or segmentally flexible such as of plastic material coupled to varying durometer plastic material or metallic material, may have an a-traumatic tip, and may be placed into the lesion prior to introduction of the device over this element, or alternatively, it may be placed through the device at a later stage, for the purpose for example, of enabling continued access to the site upon removal of the biopsy instrument. The purpose of this access could be to deliver medications, brachytherapy or other implantable items (temporary or permanent) at a later time or day, with the advantage that such access could continue well beyond the time when the more bulky biopsy instrument is removed. Such an element could be secured in place for example, under a sterile dressing for later one time or repeated use. Elements 140 and 27 may be removable and/or replaceable as desired, such as when storage capacity may be filled to maximum, or to switch to a delivery cartridge (not shown) such as shown below (e.g., cartridge 214, FIG. 39).

Figure 32:
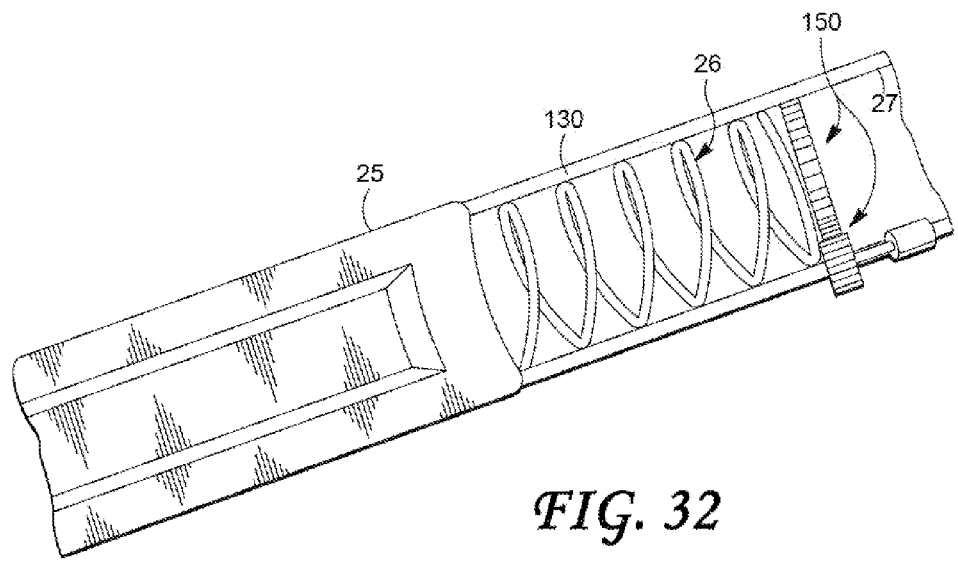
FIG. 32 is a side view of a non-rotating or differentially rotating outer tubular element of a core biopsy device, and a section such as an internal helical transport/delivery mechanism, in relationship with (a) non-rotating or differentially rotating outer tubular element(s) of a biopsy device, according to one embodiment.

FIG. 32 shows a side view of a gear drive mechanism 150, according to one embodiment, for rotating an internal helical coring/transport element 26 of FIG. 24 covered by an non-rotating (for example) outer tube 25. 25*b* illustrates a protruding key-type element that would serve to lock the outer tube to the device housing, if, for example, the outer tube happened to have a round cross-section. As shown, actuating rod(s) 130 (FIG. 28) may be housed within the tube 25, which would also be driven forward (distally) and back (proximally) with coring/transport element 26 in order to move cutting beak assembly 13. Actuating rod(s) 130 may also be placed externally to tube 25, with, for example, the beak assembly 13 in a "more than fully open" or over center (i.e., cutting tips coring a greater diameter of tissue than the outside diameter of tube 25 with external rod(s) 130) configuration to allow the external rod(s) 130 to rotate with tube 25 without binding on tissue being penetrated axially. An attachment segment of a tissue storage magazine 27 (FIG. 31) is also shown.

Figure 33:
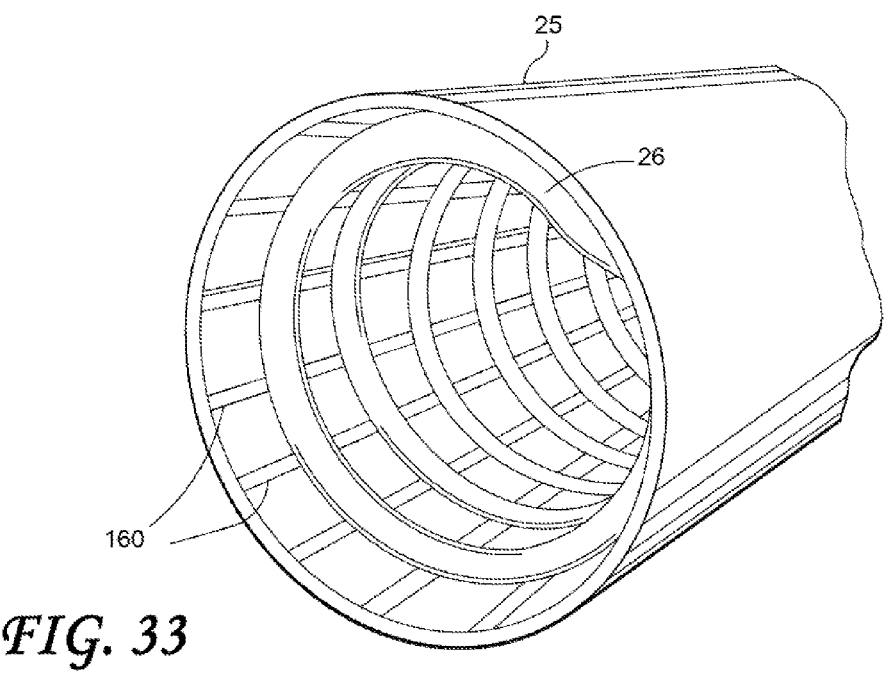
FIG. 33 is an end on, perspective view of a non-rotating or differentially rotating outer tubular element of a core biopsy device, showing an internal surface configuration, and a section such as an internal non-rotating or differentially rotating inner helical transport/delivery element in relationship together, of the present biopsy device, according to one embodiment.
Figure 34:
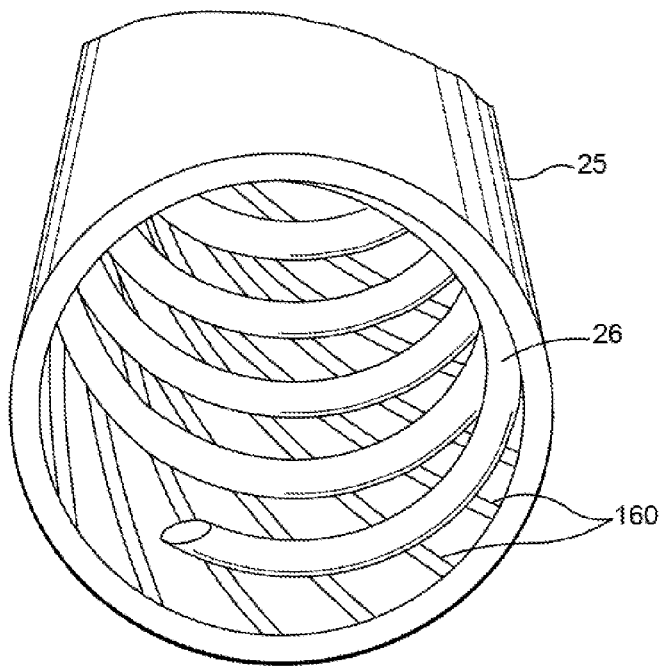
FIG. 34 is an end on, perspective view of a rifled internal surface segment of a non-rotating or differentially rotating outer tubular element with a view of an comprised internal non-rotating or differentially rotating inner transport/delivery helical element of a core biopsy device, according to one embodiment.
Figure 35:
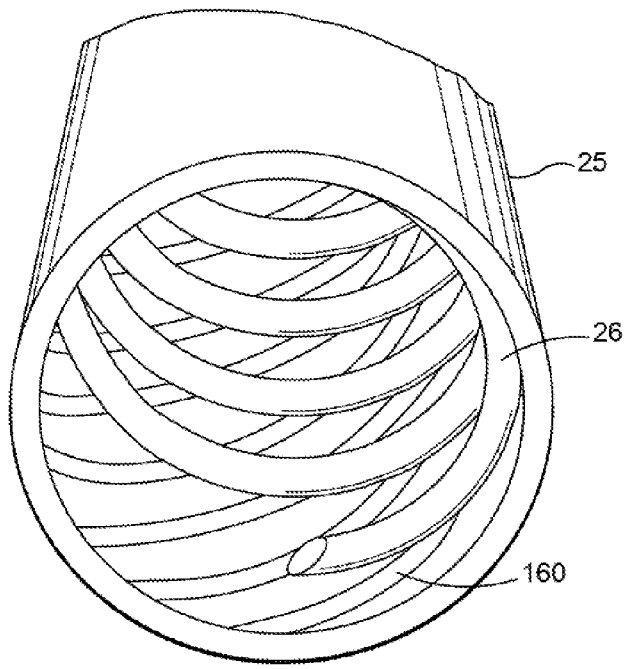
FIG. 35 is an end on, perspective view of yet another internal surface configuration of a non-rotating or differentially rotating outer tubular element with a view of an comprised internal non-rotating or differentially rotating inner transport/delivery helical element of a core biopsy device, according to one embodiment.

FIGS. 33, 34 and 35 are "down the barrel" perspectives of elements such as a non- or differentially rotating inner helical coring/transport element 26 along with outer non- or differentially rotating outer tubular element 25, according to further embodiments. These figures show varying configurations of rifling internal treatments 160 (lands, pits, grooves, raised or recessed features, and the like) or other physical treatments of the internal surface of the outer tubular element 25. The treatments such as surface treatments 160 may be configured to create a resistance to the twisting of core tissue specimen(s) such that rotation of either the outer tubular element 25 or the inner helical coring/transport element 26 would cause the core tissue specimen(s) to move in an axial direction. Inner treatments 160 as shown may be configured, according to one embodiment, as rifling grooves cut into the inner wall of an outer coring/transport tubular element 25, or may be structural ribs placed around the inside wall of tubular element 25. Additionally, or in place of the rifling grooves or other features, creating a roughened interior surface within the inner surface of the tubular element 25 in a geometrically favorable (continuous or discontinuous) way, or any another way of creating a higher friction interior surface relative to an inner helical component 26, may result in similar desired longitudinal movement of tissue specimen(s) such as from target lesion 15, urging such severed tissue core in the proximal direction within the coring/transport element 25. FIGS. 34 and 35 show other possible rifling treatment 160 configurations of internal wall features of outer tubular element 25, according to further embodiments. As described, rotation of either element 25 or 26, or differential rotation of these elements, results in the most optimal movement forces, partially depending on tissue characteristics and other factors. It is to be understood that the optimal configurations may be determined experimentally for various types of materials being transported by these mechanisms.

Figure 36:
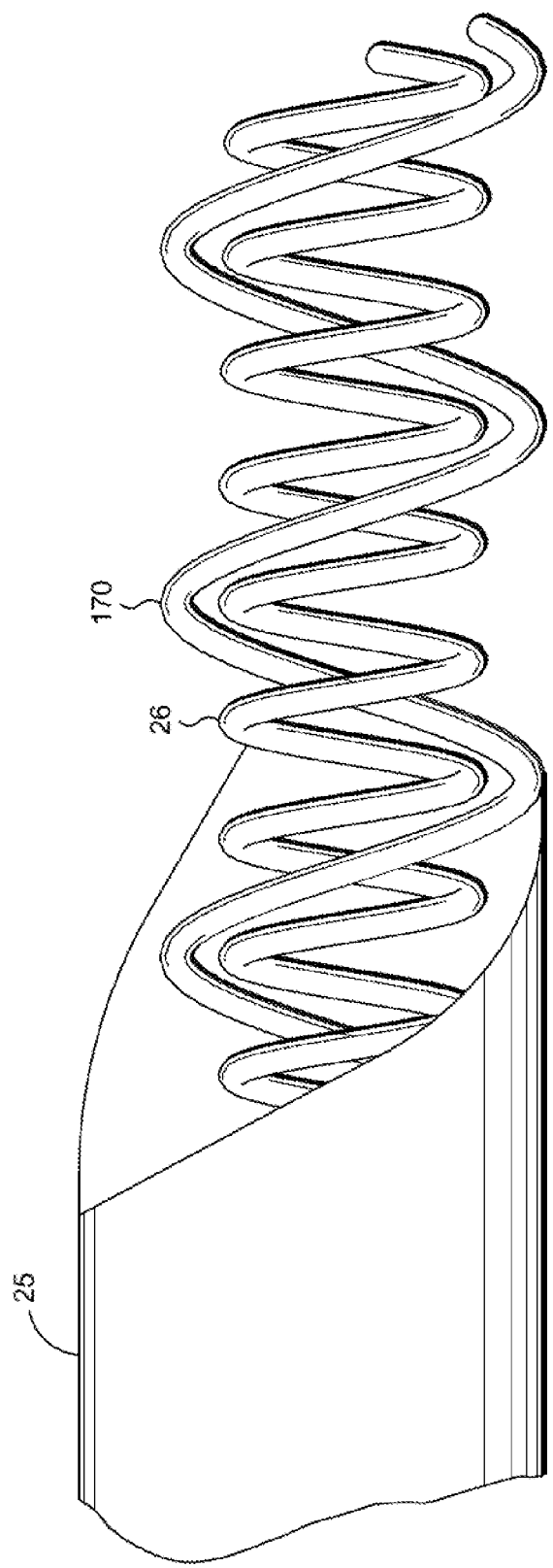
FIG. 36 is a side view of a non-rotating or differentially rotating outer tubular element of a core biopsy device, and a section such as a non-rotating or differentially rotating internal helical transport/delivery mechanism, in relationship with an additional non-rotating or differentially rotating internal helical transport/delivery element, according to one embodiment.

FIG. 36 shows yet another embodiment, provided with (an) additional internal helix or helices 170 with (a) different pitch angle(s) with respect to a more internal helical component 26. In this embodiment, helical element(s) 170 may be provided in addition to, or in place of, internal surface components and/or surface treatments such as surface treatments 160, or others that may be integral or solidly attached to coring/transport tube element 25. Utilizing a different speed or direction, or keeping one or the other helical component fixed in rotation, are exemplary actions that result in longitudinal or axial movement (e.g., proximally-directed) of (e.g., tissue) materials therein such as from target lesion 15. Additionally, this drawing illustrates the potential for use of the additional helical element or elements to act in concert or at differential rotational speeds and/or rotational direction, coupled with sharpened tips or tip edges, which if rotated at the same speed and direction, would assist tissue penetration.

Figure 37:
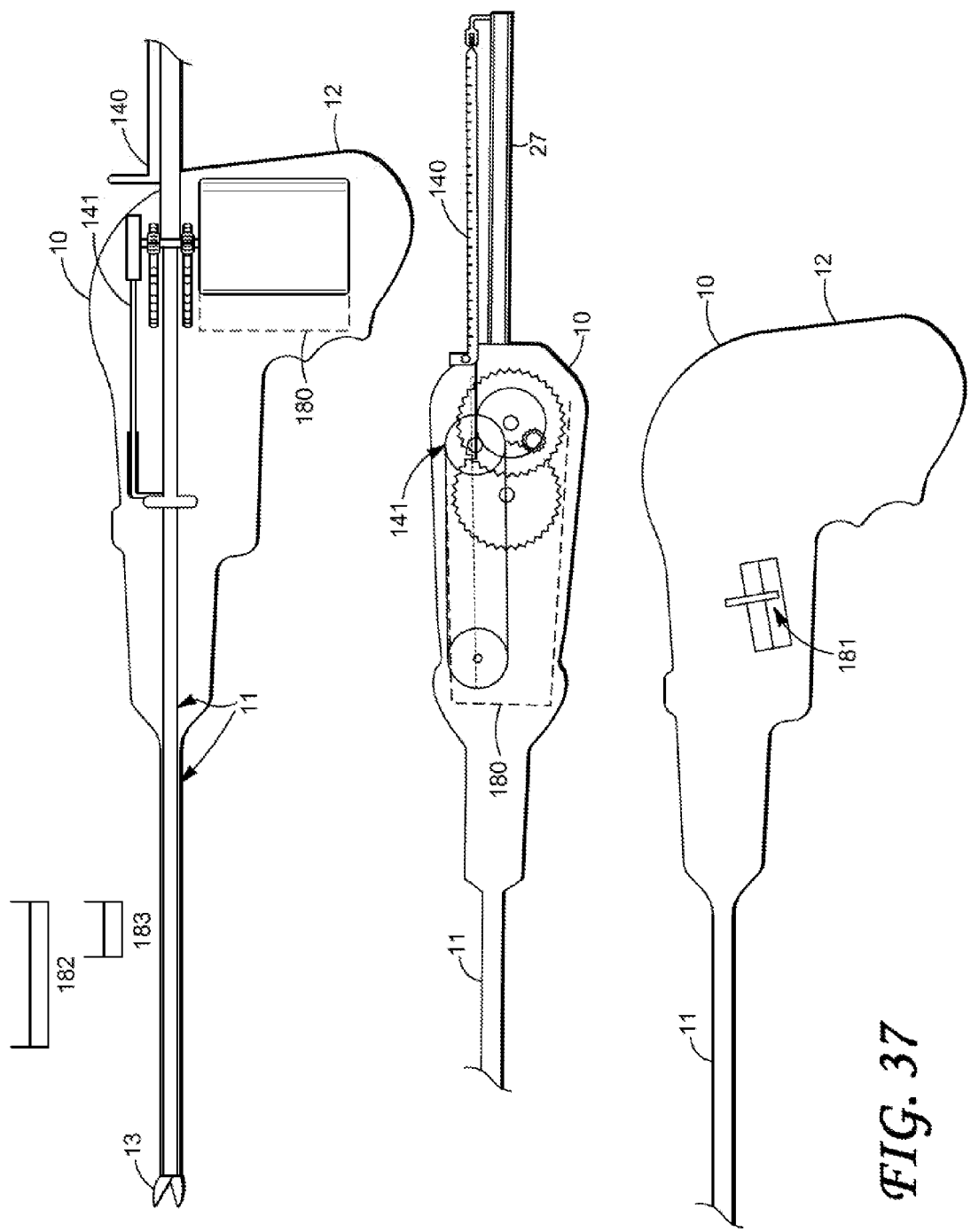
FIG. 37 shows two side views and a top view of a biopsy device, with an internal carriage that moves to a distance, or could move within such boundary 180 holding internal components, according to one embodiment.

FIG. 37 shows three views of biopsy device 10, the top and bottom of which are side views and the center view thereof being a plan view, from the top looking down, illustrating further aspects of embodiments. In this illustration, an internal carriage structure 180 is shown with carried components, including: tubular coring and transport assembly 11; cutting beak assembly 13 along with but not limited to, all needed and/or added elements for actuation, coring, transport and storage/delivery that may be movable with respect to handle 12 and its fixed activation switches (not shown); and power supply and wiring attachments (not shown) to same. In this embodiment, vacuum/delivery assemblies 140 may be fixed, rather than moved by carriage 180. One of the mechanisms for moving carriage 180 is a manual slide lever element 181 that may be used by an operator to move the carriage structure 180 manually during coring such that either a longer or shorter core specimen lengths 182, 183 may be retrieved as desired, or to prevent undesired penetration by coring elements of the present biopsy device into adjacent vulnerable structures, such as major blood vessels or other nearby organs. Alternatively, actuation of carriage 180 may be carried out via a motor, or via mechanically driven mechanisms such as a rack-and-pinion mechanism (not shown), for movement of carriage 180, including the excursion and direction of carriage 180.

These movements may easily be made operator pre-selectable, or selected in real-time (i.e., during the coring stage itself), as desired.

Figure 38:
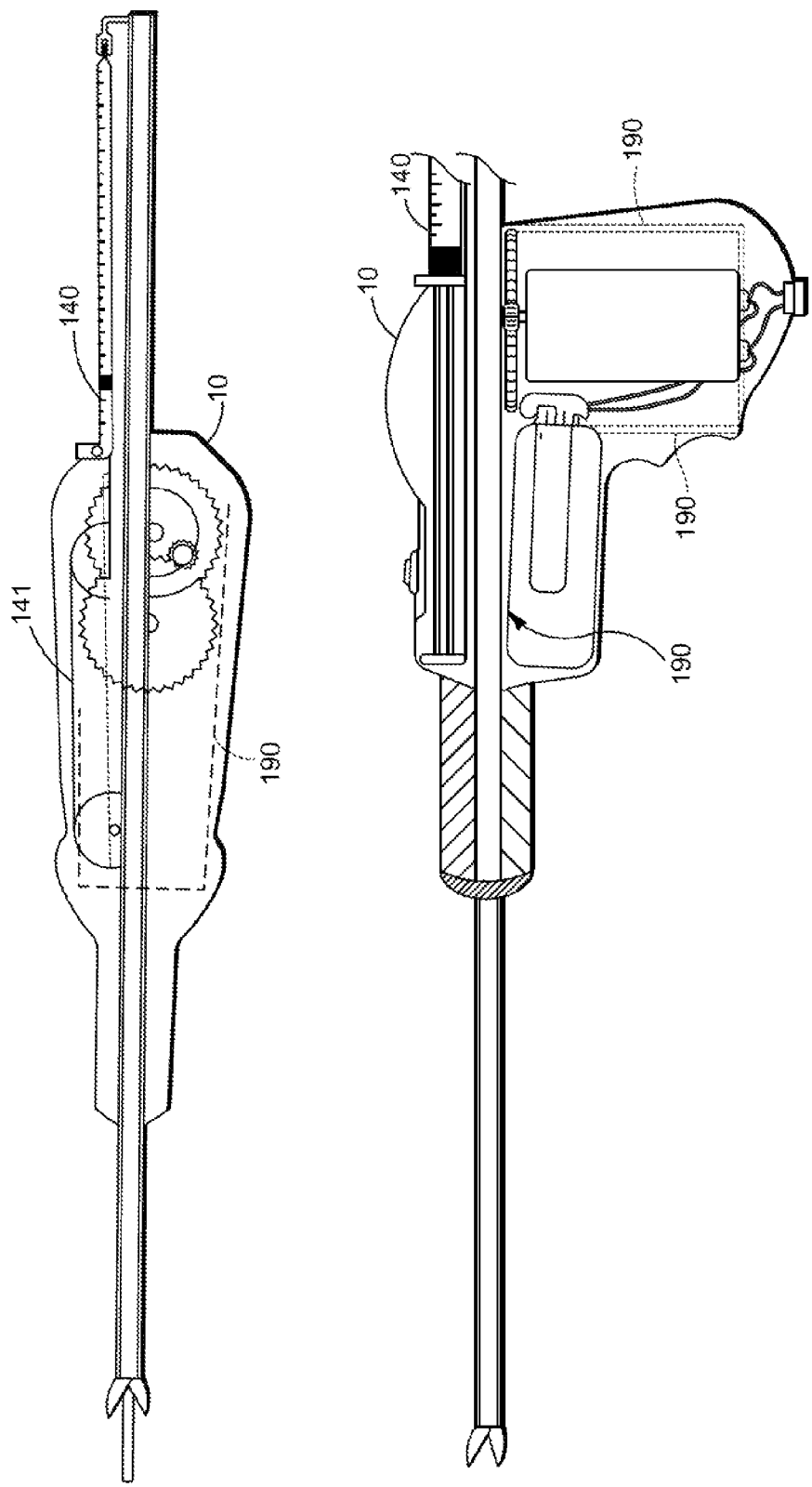
FIG. 38 is a side and top view of a biopsy device, with an internal, movable, excursion-modifying assembly (stage/carriage) 190 of components of the present biopsy device, in this case carrying additional components vacuum/delivery assembly 140, according to one embodiment.

FIG. 38 shows a side and top view of biopsy device 10, according to one embodiment, including a carriage inclusive of an alternative carriage 190, which in this case may comprise vacuum/delivery assembly 140, 141 in its frame, such that movement of carriage 190 would likewise alter their axially-directed excursions.

FIG. 39 is a side view of a biopsy device 10, according to embodiments, provided with and coupled to a collection receptacle 210 with its seal cap 211 in place and connection tube 212 unattached. Collection tube 212 may comprise a one-way valve 213 in place, and other structures designed to deliver liquids collected from the biopsy site into collection receptacle 210 without permitting fluids to be aspirated by vacuum/delivery assembly 140 by replacing filter valve 216. In this embodiment, storage magazine 27 (shown in FIG. 31) has been replaced by delivery cartridge 214 such that vacuum/delivery assembly 140 may be positioned to deliver contents of cartridge 214, which may be pre-packaged within cartridge 214. A connection tube 215 may be provided connected between vacuum/delivery assembly 140 and delivery cartridge 214, and this connection tube is depicted with a one-way filter-valve 216, acting as a delivery port to the device for addition of materials desired to be injected to the transversed tissue or in the biopsy site, opposite in functional direction compared with one-way valve 213, also, such that, for example, ambient air (optionally filtered) may be drawn in by vacuum/delivery assembly 140 to enable it to deliver contents of delivery cartridge 214 to coring and transport assembly 11 for deposition into the biopsy cavity (not shown), or into the tissues near to the area of the biopsy.

Figure 40:
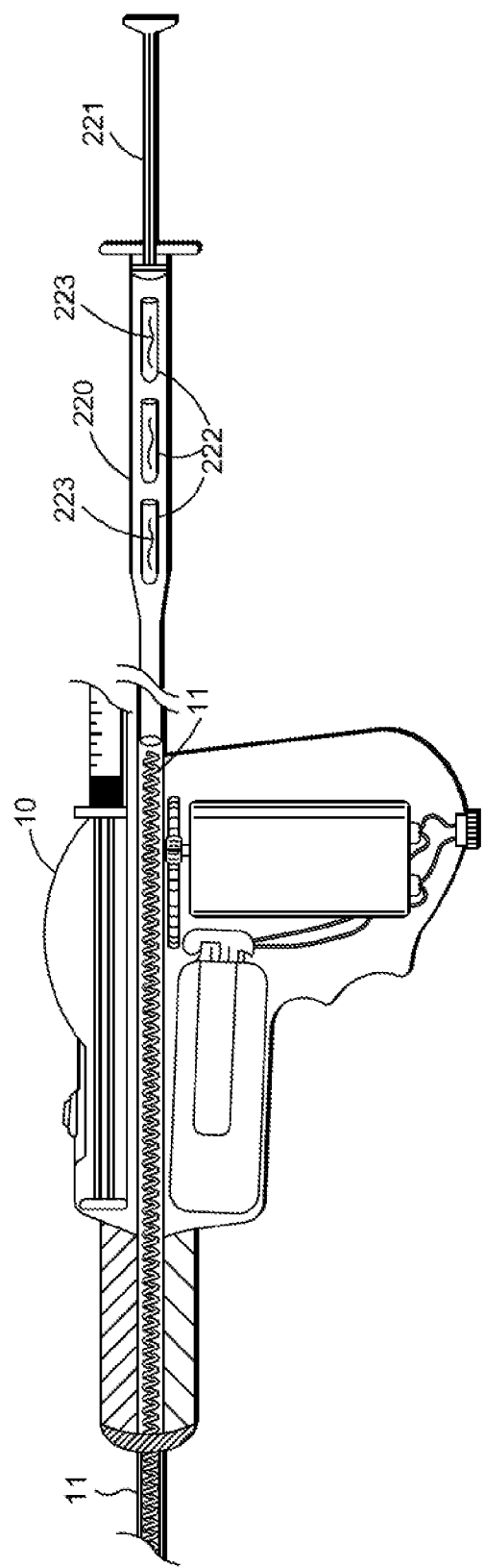
FIG. 40 is a side view of a biopsy device, showing a connected cartridge containing pellets in its barrel, according to one embodiment.

FIG. 40 is a side view of biopsy device 10, according to another embodiment, which may comprise a delivery syringe 220 connected to the biopsy device 10, such that upon depression of plunger 221 into delivery syringe 220, its contents may be delivered to coring and transport assembly 11 for delivery and deposition into or near the biopsy cavity, or, if pre-biopsy, into the tissues near the target lesion. In this illustration, reversal of the direction of rotation of tubular coring and transport assembly 11, would result in delivery distally (out the end of) out of the device into the tissue delivery site within for example the lesion or nearby breast tissues. The contents of delivery syringe 220 may comprise a variety of materials, including: pre-treatment medications, agents or other deliverables, which may be solid, semi-solid, liquid and/or gaseous in nature, radioactive, and/or combinations of these, implantable elements which may be inert for purposes of cosmetic enhancement; and marking materials for reference and other purposes. Not all of these types of elements are shown, however, solid or spongy, compressible-type pellets 222 with internal marker elements represented by 223 are depicted pictorially in FIG. 40.

The following describes aspects of the present biopsy methods, according to embodiments. In particular, described hereunder is the manner in which the closed and open beak assembly configurations and stages may be used for specific purposes, enabled by the present biopsy device's design, functionality and features. As described herein, the biopsy device 10 may be used in either or both the open and/or closed beak configurations at various times during the biopsy procedure for purposes of tracking the tip of the biopsy device 10 to a target lesion within the patient's tissue. There are specific clinical situations where it may be desirable to penetrate the tissue leading to a target in closed beak assembly configuration as shown in FIGS. 7 and 23b, or in open beak assembly configuration as shown in FIGS. 9 and 23b. A clinical example of the use of the closed beak assembly configurations of FIGS. 9 and 23b may comprise gently approaching target lesion 15 so that ultrasound guidance disturbance may be minimized. Note that in the closed beak configuration, no biopsy core may be generated or cut along the access path to the target lesion 15. A clinical need may be met in another situation whereby the target lesion may be approached in the open beak configurations of FIGS. 9 and 23. The open beak configuration enables operator of biopsy device 10 to remove, for example, a core of densely fibrous tissue to permit easy passage and minimal trauma for subsequent maneuvers of this device after an interruption or halt to the procedure (re-insertion, for example), or for passage of related catheters, devices and the like to and through the path created to the target area(s). The methods involved in utilizing these two distinctly different configurations are enabled by the designs of the rotating, cutting beak assembly 13 themselves, as well as by the ability of the biopsy device 10 to halt or interrupt stages prior to moving onward to a subsequent stage. In addition, embodiments enable de-coupling of rotation of closed beaks with progression to next stage(s). This feature enables continuous transport (while operating in "interrupted" stage configuration), as well as continuous coring/transport, limited only by the length of assembly 11 combined with the length of storage magazine element, such that cores as long as several inches may be retrieved, where clinically useful. A clinical situation where this may be desirable may comprise following a particular structure within the tissue, such as along the pathway of a diseased milk duct (not shown) in breast tissue, for example.

The present biopsy method, according to one embodiment, may image organ (such as breast) tissue and may identify the target lesion. The skin surface may be cleaned using known sterile techniques. The patient may then be draped, and (e.g., local) anesthetics may be administered as needed. Thereafter, the present biopsy device may be introduced through a small incision (e.g., a skin nick). The present biopsy device may then be placed in a penetration mode, with the distal beak 13 being either in the closed or open beak configuration. If the present biopsy device is caused to assume the closed beak configuration (rotation only stage at any desired speed, including zero), the distal beak 13 may then be advanced through the tissue, aiming towards the target lesion, stopping just short of the nearest edge of the target lesion (e.g., 2-4 mm). The present biopsy device may be caused to assume a closed or open-beak configuration at any time prior to the part-off stage. The physician may then continue advancing the present biopsy device as desired to continuously core, starting and stopping coring activity (rotation/transport) to redirect tip, and/or continue coring activity while redirecting tip. The coring may continue to create a specimen as long as desired. The part-off stage may then be carried out, and the coring/transport/part-off cycle may be completed.

The remainder of the entire biopsy cycle may be carried out as described above, keeping in mind that the present biopsy device may be caused to assume the open and closed beak configurations at any time. The above-described configurations/modes may be interrupted or maintained as often and/or as long as desired. For example, such modes may be employed as needed to follow (open beak coring/transport mode) a pathway of abnormal tissue growth, such as may be found along a duct in tissue in breast for example. The obtained information may be used in open beak configuration as a means to further correlate (and document such correlation) that specific core samples analyzed by histopathological exam are matched to specific imaged abnormalities within target area(s), utilizing the automatic recording and preservation capability inherent in the storage magazine design and intended use thereof.

Described hereunder are methods of utilizing an embodiment of the present biopsy device's carriage movement functionality and structures. The carriage structures and functionality, whether manually actuated or powered and whether used "on the fly" during the coring stage or pre-set, may be utilized to prevent unwanted distal penetration of the present biopsy device into nearby vulnerable structures. Embodiments of the present biopsy device fulfill another significant clinical need by utilizing, separately or in combination, the record keeping capability inherent in the structure of storage magazine 27 (see FIG. 3) and the structure and functionality of the carriage movement(s) to uniquely further characterize collected cores of, in this case, varying lengths, each of which may be unique to that specific core sample. This feature and/or combination of features enable(s) an operator of the present device to "mark" special areas of interest for the histopathologist. This marking can also accomplished by the present biopsy device, for example, by the injection of marker elements such as dyes, utilizing additional marking cartridges at any time or times during the procedure.

Indeed, according to one embodiment, a biopsy method may comprise imaging the organ (such as the breast) tissue and identifying the target lesion. The surface of the skin may be cleaned, using known sterile techniques. The patient may then be draped and then (e.g., local) anesthetics may then be delivered as needed. The distal beak 13 of the present biopsy may then be introduced through a small incision (e.g., skin nick). The penetration mode may then be activated, in either a closed or open beak configuration. If the closed beak configuration (rotation only stage) is employed, the distal tip beak 13 may then be advanced, aiming towards target lesion and stopping just short of the nearest edge of the target lesion (e.g., 2-4 mm). The open beak stage may be initiated at any time and interrupted prior to part-off stage. The present biopsy device may be further advanced as desired to continuously core, starting and stopping coring activity (rotation/transport) to redirect the distal beak 13, and/or continue coring activity while redirecting the distal beak 13. The coring may be continued to create as long a specimen as desired. The part-off stage may then be enabled and the coring/transport/part-off cycle may be completed. During the biopsy stage, carriage movements may be utilized as desired to safely limit (e.g., shorten or lengthen) the excursion to prevent unwanted entry of instrument tip into nearby organs and/or tissues, and/or in order to remove longer core specimen(s) to obtain more abnormal tissue, and/or for inclusion of elements of normal tissue on near or far edges of the target lesion. In either or both cases (longer/shorter specimen cores), the information obtained while carrying out carriage movements may be utilized to further characterize (and document such characterization) the tissue collected at unique lengths, thereby enabling histopathological analysis of each specimen to be positively correlated with specific imaged areas within the target lesion, utilizing the automatic recording and preservation capability inherent in the storage magazine design and intended use.

Further aspects of the use of the storage magazine 27 (shown in FIG. 3) are now described, such that various clinical needs may be fulfilled by permitting the operator of the present biopsy device to inspect the core samples more closely, and in some cases tactilely, without destroying the record keeping function of storage magazine 27, FIG. 3. Additional method of ex-vivo imaging are also described, as are the samples in the order in which they were received and stored within storage/record keeping storage magazine 27, according to still further embodiments. Since storage magazines, according to embodiments, may be configured to be removable and/or replaceable at any time(s) during the procedure, the present biopsy device enables a variety of procedural methods to ensue which would not be possible, or at least would be impractical, without the structures disclosed herein. For example, using the present biopsy device, a clinician may segregate the contents of one storage magazine from the contents of another, additional storage magazine. The operator of the present biopsy device may also have the ability to interrupt coring/transport/storage with another function of biopsy device, all the while, at operator's discretion, keeping the present biopsy device's shaft coring and transport assembly 11 in place, thus minimizing trauma associated with repeated removal and insertion of these elements of the present biopsy device.

Indeed, according to one embodiment, a tissue biopsy method may comprise performing coring/biopsy/transport cycles as described above. Thereafter, the procedure may be completed by removing the storage magazine and/or proceeding to marking and/or treatment phases. The storage magazine may then be removed and, if desired, placed under X-Ray, magnetic resonance imaging and/or ultrasound transducer or high resolution digital camera if the storage magazine is made of a transparent material. The core tissue specimens may then be imaged/recorded. The magazine may then be placed in a delivery receptacle, sealed and delivered to a lab for further analysis, making note of core lengths and correlating with imaging record(s) in-situ and ex-vivo. Upon removal of storage magazine from the present biopsy device, the collected cores may then be visually inspected through the transparent walls of the magazine. The magazine may then be split open to tactilely analyze the tissue specimens as desired. The magazine may then be closed again, with the specimen therein. The magazine may then be deposited in a transport receptacle, sealed and delivered to a lab.

The storage magazine may then be replaced with additional empty storage magazine(s) as needed to complete the biopsy procedure. Alternatively, other cartridges/magazines may be fitted to the present biopsy device to deliver medications, markers and/or tracer elements, therapeutic agents, or therapeutic and/or cosmetic implants to the biopsy site. The procedure may then be terminated or continued, such as would be the case should the practitioner desire to biopsy/core other nearby areas as deemed clinically useful.

The present biopsy device may be formed of or comprise one or more biocompatible materials such as, for example, stainless steel or other biocompatible alloys, and may be made of, comprise or be coated with polymers and/or biopolymeric materials as needed to optimize function(s). For example, the cutting elements (such as the constituent elements of the beak assembly 13) may comprise or be made of hardened alloys and may be additionally coated with a slippery material or materials to thereby optimize passage through living tissues of a variety of consistencies and frictions. Some of the components may be purposely surface-treated differently with respect to adjacent components, as detailed herein in reference to the transporting tubular and storage components. The various gears may be made of any suitable, commercially available materials such as nylons, polymers such as moldable plastics, and others. If used, the motor powering the various powered functions of the present biopsy device may be a commercially available electric DC motor. The handle of the present biopsy device may likewise be made of or comprise inexpensive, injection-molded plastic or other suitable rigid, easily hand held strong and light-weight material. The handle may be configured in such a way as to make it easily adaptable to one of any number of existing guiding platforms, such as stereotactic table stages. The materials used in the present biopsy device may also be carefully selected from a ferromagnetic standpoint, such that the present biopsy device maintains compatibility with magnetic resonance imaging (MRI) equipment that is commonly used for biopsy procedures. The vacuum/delivery assembly components may comprise commercially available syringes and tubing for connecting to the present biopsy device, along with readily available reed valves for switching between suction and emptying of materials such as fluids which may be suctioned by the vacuum components. The fluids collected by the embodiments of the present biopsy device in this manner may then be ejected into an additional external, yet portable, liquid storage vessel connected to the tubing of the present biopsy device, for discarding or for safe keeping for laboratory cellular analysis.

The power source may comprise an external commercially available AC to DC transformer approved for medical device use and plugged into the provided socket in the present biopsy device, or may comprise an enclosed battery of any suitable and commercially available power source. The battery may be of the one-time use disposable (and optionally recyclable) variety, or may be of the rechargeable variety.

The cutting beak assembly of embodiments of the biopsy devices may be used, without alteration of their shape, attachment or any other modification, to penetrate tissue on approach to a target lesion. The cutting beak assembly may then be used to open and core the tissue specimen, and to thereafter part-off the specimen at the end of the coring stage. The beak assembly may also be used to help augment transport of the collected specimen. Having such multiple functions integrated in a single device saves valuable cross-sectional area, which in turn creates a device that has a minimal outer diameter while providing the maximum diameter core sample. Maximizing the diameter of the core sample is believed to be significant from a clinical standpoint, since it has been demonstrated in multiple peer-reviewed journals that larger diameter core specimens yield more accurate diagnoses. The clinical desire for large diameter core samples, however, must be balanced against the trauma associated with larger caliber devices. Embodiments optimize the ratio so that the clinician can have the best of both worlds. Advantageously, according to one embodiment, the internal helical transport system may be configured to augment the coring function of the forward cutting beaks. The helical transport coring elements may be configured to apply gentle, predictable traction on the cored specimen, during and after coring, which permits pairing the ideal speed of longitudinal excursion of the coring elements of the present biopsy device with the ideal speed of rotational movement of the same elements. In this manner, the architecture of the collected specimen is less likely to be disrupted during transport. It has been shown in peer-reviewed scientific articles that preserving tissue architecture (i.e., preserving the architecture of the tissue as it was in vivo) to the extent possible leads to an easier and more accurate diagnosis. The present vacuum/delivery mechanism may be configured to enable the force of vacuum to be exerted directly to the coring transport components, such that coring and transport of the specimen is handled as delicately, yet as surely, as possible and comprises non-significantly dimension-increasing components such as progressively sized fenestration features within collection magazine areas. If the present biopsy device were to rely solely on vacuum for tissue transport, then vacuum artifact, which is a known and described phenomenon associated with conventional biopsy devices, might be present to a greater degree than is present (if at all) in embodiments described herein. On the other hand, were embodiments of the present biopsy device to rely solely on a physical pushing or pulling mechanism to retrieve cut specimen samples, crush artifact might be more prominent than is otherwise present when embodiments of the present biopsy device and methods are used.

Turning now to yet further structures of embodiments, the carriage element provides structure within the handle of the present biopsy device for locating the various internal drive components, and gives the operator the ability to move this carriage with its components as a unit, enabling the operator to advantageously vary the core length in real time, (i.e., during the procedure), with a mechanical arrangement coupled to the present biopsy device that may be selected to be powered manually or by an internal or external motor. The presence of a cut-off switch enables the operator to selectively choose a continuous operation function, which permits rapid yet controllable repeatable biopsy cycles. By enabling such a functional option, procedure times can be minimized, which may be a potential advantage since tissue images may become more obscure with increasing procedure times as fluids accumulate at the site.

Embodiments are highly portable and require minimal supporting equipment, especially in battery-operated or mechanically-powered embodiments. For mechanically-powered embodiments, one or more "wind-up" springs may provide the mechanical power required by the present biopsy device. Advantageously, such embodiments may find widespread acceptance and use throughout the world, particularly in the more economically-disadvantaged areas where access to disposable batteries may be difficult, or where mains power may be unreliable. Many conventional devices designed for the purpose of tissue biopsy need, by their design limitations, far more external supporting mechanisms, such as external drive systems, external fluid management and tissue management systems, as well as separate power and delivery systems, all of which may be built in features of the embodiments illustrated and described herein.

The internal surface treatments of an outer tube and a hollow, helical inner component, when acting in concert, move materials in a variety of phase states along longitudinally without the need for complex components that would otherwise contribute substantially to the outer caliber dimensions of the present biopsy device. Embodiments comprise a hollow helical transport mechanism that may be both strong and flexible, which continues to function even when distorted by bending. Conventional biopsy devices typically cease to function properly if distorted even slightly. As such, the present biopsy device may be configured to define a curve along its longitudinal axis and would still function properly, with minimal modifications.

Advantageously, a biopsy and coring device, according to embodiments, comprises features configured to perform medical core biopsy procedures or for harvesting tissue for other uses. These features comprise structures configured for penetration, coring, part-off, transport and storage of core specimens for medical purposes such as diagnosis and treatment of a variety of diseases and abnormalities. Integral and detachable components may be provided and configured to aspirate fluids for cellular analysis as well as deliver agents at various selectable stages of the procedure. The present biopsy device may be selectable for automatic and/or semi-automatic function, may be used with or without image guidance, and may be compatible with a variety of guidance imaging equipment such as ultrasound, magnetic resonance imaging and X-ray imaging. The present biopsy device may be configured to be disposable and/or recyclable, highly portable, and delivered for use in sterile packaging, typical of medical devices having contact with internal body structures. The present biopsy device may be configured to be minimally invasive; may be configured to collect maximum diameter tissue specimen cores in operator selectable lengths as gently as possible so as to preserve gross anatomic, cellular and sub-cellular architectures, thereby maintaining the integrity of the overall structures and makeup of the samples themselves as well as their relationships with comprised normal adjacent segments of tissue in the core samples so that transition areas can also be used for analysis; and may be configured to deliver the samples reliably to a storage receptacle for sequential recording and easy retrieval therefrom, so that the biopsy specimens can be analyzed as accurately and easily as possible. As embodied herein, the present biopsy device comprises several features that may be therapeutic in nature, to be utilized at various stages along the diagnosis/treatment pathway.

Embodiments are not limited in their utility and applicability to biopsy-related applications. For example, the hollow helical transport component may be used in many commercial/industrial applications where handling a variety or single-type material(s) is/are desirable, potentially on a much larger scale than is the case in medical biopsy procedures. Since the present devices can function around corners for example, the present biopsy devices may be made far more compactly than other linearly-configured devices made for the same or similar purposes. Embodiments may also reliably function to core and/or transport under extreme conditions that may be difficult to control such as shifting surroundings and other factors. It is to be noted, moreover, that the distal tip and/or body of the present biopsy device may be configured to be steerable without loss of functionality, which may have uses both within and outside of the medical field. Additionally, the length of the barrel assembly portion (including, for example, the tubular coring and transport assembly 11) of embodiments of the present biopsy devices may be configured to have most any length, and to have a variety of shapes, such that embodiments might find utility in remote applications, some of which may require traversal of multiple curves, which may themselves be fixed in nature or moving, again, without adversely affecting the performance of the present biopsy device. It is to be noted that individual elements and sub-systems of embodiments have separate utility and may advantageously be deployed in other devices configured for other purposes. Indeed, the depiction and description of the embodiments herein is not meant to convey that such separate elements, sub-systems, assemblies and mechanisms do not have novelty and utility outside of the field of medical biopsies. For example, elements such as the rotating, cutting elements of beak assembly may perform their intended function(s) without the other components described herein and should not be assumed to be dependent on some of the other features in order to function as intended.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A biopsy device, comprising:
a hollow shaft comprising a longitudinal lumen of a first diameter that defines a first radius of curvature;
a beak assembly disposed at a distal end of the hollow shaft, the beak assembly comprising a first articulated movable cutting element and a second articulated movable cutting element, each of the first and second articulated movable cutting elements comprising a proximal portion and a distal portion that is narrower than the proximal portion, and comprising an outer surface and an inner surface, the inner surfaces of the first and of the second articulated movable cutting elements having the first radius of curvature from a proximal-most end to a distal most end thereof, the beak assembly being configured to rotate and assume at least a first configuration in which the first and second articulated movable cutting elements are operative to cut a core of a second diameter that is greater than the first diameter through tissue and a second configuration in which the first and second articulated movable cutting elements are operative to cut and move through the tissue and to sever the core; and
a helical tissue transport element disposed within the hollow shaft and configured to transport the core through the hollow shaft as the hollow shaft compresses the core, the helical tissue transport element being coupled to the beak assembly and configured to cause the first and second articulated cutting elements to move between the first and second configurations.

2. The biopsy device of claim 1, wherein the first configuration is an open configuration in which the first and second articulated movable cutting elements are controlled to open wider than the first diameter and wherein the second configuration is a closed configuration in which the first and second articulated movable cutting elements are controlled to close to present a tapered profile.

3. The biopsy device of claim 1, further comprising a source of vacuum coupled to the hollow shaft.

4. The biopsy device of claim 1, further comprising a first hinge coupled at least to the first articulated movable cutting element and a second hinge coupled at least to the second articulated movable cutting element, the first and second hinges being disposed at a distal end of the hollow shaft.

5. The biopsy device of claim 4, wherein edges of the first and second hinges are sharpened.

6. The biopsy device of claim 4 wherein, in the first configuration, distal-most tips of the first and second hinges are spaced away from one another by a distance that is greater than the first diameter.

7. The biopsy device of claim 1, wherein the beak assembly defines an asymmetrical shape.

8. A method of performing a biopsy, comprising:
introducing, into tissue, a biopsy device comprising a hollow shaft comprising a longitudinal lumen of a first diameter that defines a first radius of curvature, a helical tissue transport element disposed for rotation within the hollow shaft, and a beak assembly coupled to a distal end of the hollow shaft and coupled to the helical tissue transport element, the beak assembly comprising a first articulated movable cutting element and a second articulated movable cutting element, each of the first and second articulated movable cutting elements comprising a proximal portion and a distal portion that is narrower than the proximal portion, and comprising an outer surface and an inner surface, the inner surfaces of the first and of the second articulated movable cutting elements having the first radius of curvature from a proximal-most end to a distal most end thereof;
advancing the hollow shaft through the tissue while rotating the beak assembly in a first configuration in which the first and second articulated movable cutting elements are operative to cut a core from the tissue, the core having a second diameter that is greater than the first diameter;
acting upon the helical tissue transport element to cause the beak assembly to assume a second configuration in which the first and second articulated movable cutting elements are operative to sever the core; and
compressing the core within the hollow shaft and transporting the compressed core within the hollow shaft using the helical tissue transport element.

9. The method of claim 8, wherein the first configuration is an open configuration in which the first and second articulated movable cutting elements are controlled to open wider than the first diameter and wherein the second configuration is a closed configuration in which the first and second cutting elements are controlled to close to present a tapered profile.

10. The method of claim 8, further comprising coupling a source of vacuum to the hollow shaft.

11. The method of claim 8, wherein the introducing is carried out with the beak assembly being in the second configuration.

12. The method of claim 8, wherein the compressing the core comprises urging the severed core into the longitudinal lumen of the hollow shaft.

13. The method of claim 12, wherein the urging the severed core into the longitudinal lumen of the hollow shaft is carried out at least in part by the tissue transport assembly.

14. The method of claim 8, wherein the biopsy device further comprises an internal helix element configured axially to the helical tissue transport element and configured to transport tissue in a proximal direction within the hollow shaft and wherein the method comprises rotating the helical tissue transport element at a first rotational speed and rotating the internal helix element at a second rotational speed that is different than the first rotational speed.

* * * * *